（12）United States Patent
Eon-Duval et al.

US008513393B2

(10) Patent No.: US 8,513,393 B2
(45) Date of Patent: *Aug. 20, 2013

(54) PROCESS FOR THE PURIFICATION OF FC-CONTAINING PROTEINS

(75) Inventors: Alex Eon-Duval, Vevey (CH); Alain Lamproye, Bouloz (CH)

(73) Assignee: Ares Trading S.A., Aubonne (CH)

( * ) Notice: Subject to any disclaimer, the term of this patent is extended or adjusted under 35 U.S.C. 154(b) by 416 days.

This patent is subject to a terminal disclaimer.

(21) Appl. No.: 12/377,122

(22) PCT Filed: Aug. 27, 2007

(86) PCT No.: PCT/EP2007/058887
§ 371 (c)(1),
(2), (4) Date: Apr. 6, 2010

(87) PCT Pub. No.: WO2008/025748
PCT Pub. Date: Mar. 6, 2008

(65) Prior Publication Data
US 2010/0190961 A1    Jul. 29, 2010

(51) Int. Cl.
*A23J 1/00* (2006.01)
*C07K 1/00* (2006.01)

(52) U.S. Cl.
USPC .......................... 530/416; 530/412; 530/413

(58) Field of Classification Search
None
See application file for complete search history.

(56) References Cited

U.S. PATENT DOCUMENTS

| | | | |
|---|---|---|---|
| 5,447,851 A * | 9/1995 | Beutler et al. | 435/69.7 |
| 5,593,675 A * | 1/1997 | Hodler et al. | 424/130.1 |
| 5,969,102 A | 10/1999 | Bram et al. | |
| 6,417,335 B1 * | 7/2002 | Basey et al. | 530/387.1 |
| 7,501,497 B2 * | 3/2009 | Rixon et al. | 530/387.3 |
| 7,635,767 B2 * | 12/2009 | Rixon et al. | 536/23.4 |
| 7,862,814 B2 * | 1/2011 | Rixon et al. | 424/133.1 |
| 7,951,919 B2 * | 5/2011 | Rixon et al. | 530/387.3 |
| 7,964,711 B2 * | 6/2011 | Rixon et al. | 536/23.4 |
| 8,168,185 B2 * | 5/2012 | Eon-Duval et al. | 424/133.1 |
| 2002/0081296 A1 | 6/2002 | Theill et al. | |
| 2002/0115175 A1 | 8/2002 | Black et al. | |
| 2003/0103986 A1 | 6/2003 | Rixon | |
| 2003/0229212 A1 | 12/2003 | Fahrner et al. | |
| 2005/0032174 A1 | 2/2005 | Peters et al. | |
| 2005/0107594 A1 | 5/2005 | Sun et al. | |
| 2007/0072307 A1* | 3/2007 | Godavarti et al. | 436/518 |

FOREIGN PATENT DOCUMENTS

| | | |
|---|---|---|
| EP | 1230354 B2 | 1/2004 |
| EP | 1084136 B1 | 8/2004 |
| EP | 1 561 756 A1 | 8/2005 |
| EP | 1 614 693 A1 | 11/2006 |
| WO | 91/03553 | 3/1991 |
| WO | 94/06476 | 3/1994 |
| WO | 96/41624 | 12/1996 |
| WO | 98/39361 | 9/1998 |
| WO | 00/40716 | 7/2000 |
| WO | 02/094852 | 11/2002 |
| WO | 03/059935 A2 | 7/2003 |
| WO | 2004/076485 A1 | 9/2004 |
| WO | 2005/100394 A2 | 10/2004 |
| WO | 2005/044856 | 5/2005 |
| WO | 2005/047337 A1 | 5/2005 |
| WO | 2006/099308 A2 | 9/2006 |
| WO | WO 2006/110277 A1 * | 10/2006 |

OTHER PUBLICATIONS

Akerstrom, B., et al., "Protein L: An Immunoglobulin Light Chain-Binding Bacterial Protein," The Journal of Biological Chemistry, vol. 264, No. 33, pp. 19740-19746 (1989).
Altschul, S., et al., "Basic Local Alignment Search Tool," J. Mol. Biol., vol. 215, pp. 403-410 (1990).
Altschul, S., et al., "Gapped BLAST and PSI-BLAST: A New Generation of Protein Database Search Program," Nucleic Acids Research, vol. 25, No. 17, pp. 3389-3402 (1997).
Armour, K., et al., "Recombinant Human IgG Molecules Lacking Fcγ Receptor I Binding and Monocyte Triggering Activities," Eur. J. Imunol., vol. 29, pp. 2613-2624 (1999).
Boschetti, E., et al., "Separation of Antibodies by Liquid Chromatography," Handbook of Bioseparation, vol. 2, Edn. 1 (ed. S. Ahuja) pp. 536-632 Academic Press, San Diego (2000).
Bossen, C., et al., "Interactions of Tumor Necrosis Factor (TNF) and TNF Receptor Family Members in the Mouse and Human," The Journal of Biological Chemistry, vol. 281, No. 20, pp. 13964-13971 (2006).
Carter, Paul J., "Potent Antibody Therapeutics By Design," Nature Reviews, Immunology, vol. 6, pp. 343-357 (2006).
Devereux, J., et al., "A Comprehensive Set of Sequence Analysis Programs for the VAX," Nucleic Acids Research, vol. 12, No. 1, pp. 387-395 (1985).
Giovannini, R., et al., "Isolation of a Recombinant Antibody from Cell Culture Supernatant: Continuous Annular Versus Batch and Expanded-Bed Chromatography," Biotechnol Bioeng, vol. 73, pp. 522-529 (2001).
Grantham, R., "Amino Acid Difference Formula to Help Explain Protein Evolution," Science, vol. 185, pp. 862-864 (1974).
Gross, J., et al., "TACI and BCMA are Receptors for a TNF Homologue Implicated in B-Cell Autoimmune Disease," Nature, vol. 404, pp. 995-999 (2000).
Hinton, P., et al., "Engineered Human IgG Antibodies with Longer Serum Half-lives in Primates," The Journal of Biological Chemistry, vol. 279, No. 8, pp. 6213-6216 (2004).
Idusogie, E., et al., "Engineered Antibodies with Increased Activity to Recruit Complement," The Journal of Immunology, vol. 166, pp. 2571-2575 (2001).
Idusogie, E., et al., "Mapping of the C1q Binding Site on Rituxan, a Chimeric Antibody with a Human IgG1 Fc," The Journal of Immunology, vol. 164, pp. 4178-4184 (2000).
International Search Report of PCT/EP207/058886 dated Nov. 13, 2007.
International Search Report of PCT/EP207/058887 dated Nov. 7, 2007.
Li, Feng., et al., "Current Therapeutic Antibody Production and Process Optimization," Bioprocessing Journal, pp. 1-8 (Sep./Oct. 2005).

(Continued)

*Primary Examiner* — Daniel E Kolker
*Assistant Examiner* — James Rogers
(74) *Attorney, Agent, or Firm* — Morgan, Lewis & Bockius LLP

(57) ABSTRACT

The invention relates to a process for reducing the concentration of free Fc-moieties in a fluid comprising an Fc-containing protein comprising a cation exchange chromatography step.

29 Claims, 1 Drawing Sheet

(56) References Cited

OTHER PUBLICATIONS

Locksley, R., et al., "The TNF and TNF Receptor Superfamilies: Integrating Mammalian Biology," Cell, vol. 104, pp. 487-501 (2001).

Moore, P., et al., "BLyS: Member of the Tumor Necrosis Factor Family and B Lymphocyte Stimulator," Science, vol. 285, pp. 260-263 (1999).

Naismith, J., et al., "Modularity in the TNF-Receptor Family," TIBS 23, pp. 74-79 (1998).

Novak, A., et al., "Expression of BCMA, TACI, and BAFF-R in Multiple Myeloma: A Mechanism for Growth and Survival," Blood, vol. 103, No. 2, pp. 689-694 (2004).

Pearson, William, "Rapid Sequence Comparison," Methods in Enzymology, vol. 183, pp. 63-67 (1990).

Porath, J., et al., "Immobilized Metal Ion Affinity Adsorption and Immobilized Metal Ion Affinity Chromatography of Biomaterials. Serum Protein Affinities for Gel-Immobilized Iron and Nickel Ions," Biochemistry, vol. 22, pp. 1621-1630 (1983).

Porath, J., et al., "Metal Chelate Affinity Chromatography, a New Approach to Protein Fractionation," Nature, vol. 258, pp. 598-599 (1975).

Shepard, S., et al., "Discoloration of Ceramic Hydroxyapatite Used for Protein Chromatography," Journal of Chromatography A, vol. 891, pp. 93-98 (2000).

Shields, R., et al., "High Resolution Mapping of the Binding Site on Human IgG1 for FcγRI, FcγRII, FcγRIII, and FcRn and Design of IgG1 Variants with Improved Binding to the FcγR*" The Journal of Biological Chemistry, vol. 276, No. 9, pp. 6591-6604 (2001).

Stanker, L., et al., "One-Step Purification of Mouse Monoclonal Antibodies from Ascites Fluid by Hydroxylapatite Chromatography," Journal of Immunological Methods, vol. 76, pp. 157-169 (1985).

Steurer, W., et al., "Ex Vivo Coating of Islet Cell Allografts with Murine CTLA4/Fc Promotes Graft Tolerance," The Journal of Immunology, vol. 155, pp. 1165-1774 (1995).

Tarditi, L., et al., "Selective High-Performance Liquid Chromatographic Purification of Bispecific Monoclonal Antibodies," Journal of Chromatography, vol. 599, pp. 13-20 (1992).

Vaccaro, C., et al., Engineering the Fc Region of Immunoglobulin G to Modulate in vivo Antibody Levels, Nature Biotechnology, vol. 23, No. 10, pp. 1283-1288 (2005).

Vigers, G., et al., "Crystal Structure of the Type-I Interleukin-1 Receptor Complexed with Interleukin-1β," Nature, vol. 386, pp. 190-194 (1997).

Vola, R., et al., "Comparison of Two Different HPLC Hydroxylapatite Matrices for Resolution of IgG Idiotypes," BioTechniques, vol. 14, No. 4, pp. 650-655 (1993).

von Bulow, Gotz-Ulrich, et al., "NF-AT Activation Induced by a CAML-Interacting Member of the Tumor Necrosis Factor Receptor Superfamily," Science, vol. 278, pp. 138-141 (1997).

Xia, Xing-Zhong, et al., "TACI Is a TRAF-Interacting Receptor for TALL-1, a Tumor Necrosis Factor Family Member Involved in B Cell Regulation," J. Exp. Med., vol. 192, No. 1, pp. 137-143 (2000).

Scopes, R.K., "Protein Purification Principles and Practice," 3rd Ed., Springer-Verlag, NY, Chapters 6.1-6.2 (1994).

U.S. Appl. No. 12/377,119—Restriction Requirement dated Jun. 8, 2012.

U.S. Appl. No. 12/377,119—Non-final office action dated Aug. 1, 2012.

Fisher, et al., Treatment of Septic Shock with the Tumor Necrosis Factor Receptor: Fc Fusion Protein, The New England Journal of Medicine, vol. 334, No. 26, pp. 1697-1702 (1996).

Follman, et al., Factorial Screening of Antibody Purification Processes Using Three Chromatography Steps Without Protein A, Journal of Chromatography A, vol. 1024, pp. 79-85 (2004).

Bodmer, J., et al., "The Molecular Architecture of the TNF Superfamily," Trends in Biochemical Sciences, vol. 27, No. 1 pp. 19-26 (2002).

Boschetti, E., et al., "Bioprocess Tutorial Hydrophobic Charge-Induction Chromatography," Genetic Engineering, vol. 20, No. 13, pp. 1-4 (Jul. 2000).

Hymowitz, S., et al., "Structures of APRIL-Receptor Complexes," vol. 280, No. 8, pp. 7218-7227 (2005).

Melchers, F., "Actions of BAFF in B Cell Maturation and its Effects on the Development of Autoimmune Disease," Ann Rheum Dis., vol. 62, (Suppl II) pp. ii25-ii27 (2003).

Moreaux, J., et al., "BAFF and APRIL Protect Myeloma Cells From Apoptosis Induced by Interleukin 6 Deprivation and Dexamethasone," Blood, vol. 103, No. 8, pp. 3148-3157 (2004).

\* cited by examiner

SEQUENCE LISTING

```
<160> NUMBER OF SEQ ID NOS: 7

<210> SEQ ID NO 1
<211> LENGTH: 40
<212> TYPE: PRT
<213> ORGANISM: artificial sequence
<220> FEATURE:
<221> NAME/KEY: source
<223> OTHER INFORMATION: /note=description of artificial sequence:
      consensus sequence, in which the specific amino acids at positions
      3, 12, 14, 15, 18, 21, 25, 34 and 38 are spaced by any amino acid
<220> FEATURE:
<221> NAME/KEY: variant
<222> LOCATION: (1)..(2), (4)..(11), 13, (16)..(17),
      (19)..(20), (22)..(24), (26)..(33), (35)..(37) and (39)..(40)
      <223<   Xaa can be any naturally occurring amino acid

<400> SEQUENCE: 1

Xaa Xaa Cys Xaa Xaa Xaa Xaa Xaa Xaa Xaa Xaa Asp Xaa Leu Leu Xaa
1               5                   10                  15

Xaa Cys Xaa Xaa Cys Xaa Xaa Xaa Cys Xaa Xaa Xaa Xaa Xaa Xaa Xaa
            20                  25                  30

Xaa Cys Xaa Xaa Xaa Cys Xaa Xaa
        35                  40

<210> SEQ ID NO 2
<211> LENGTH: 293
<212> TYPE: PRT
<213> ORGANISM: homo sapiens
```

-continued

<400> SEQUENCE: 2

```
Met Ser Gly Leu Gly Arg Ser Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
        50                  55                  60

Phe Cys Arg Ser Leu Ser Cys Arg Lys Glu Gln Gly Lys Phe Tyr Asp
65              70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290
```

<210> SEQ ID NO 3
<211> LENGTH: 251
<212> TYPE: PRT
<213> ORGANISM: artificial sequence
<220> FEATURE:
<221> NAME/KEY: source
<223> OTHER INFORMATION: /note=description of artificial sequence: this
      is a portion of a human immunoglobulin heavy chain

<400> SEQUENCE: 3

```
Met Lys His Leu Trp Phe Phe Leu Leu Leu Val Ala Ala Pro Arg Trp
1               5                   10                  15

Val Leu Ser Glu Pro Lys Ser Ser Asp Lys Thr His Thr Cys Pro Pro
            20                  25                  30

Cys Pro Ala Pro Glu Ala Glu Gly Ala Pro Ser Val Phe Leu Phe Pro
        35                  40                  45
```

Pro Lys Pro Lys Asp Thr Leu Met Ile Ser Arg Thr Pro Glu Val Thr
50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
                115                 120                 125

Asn Lys Ala Leu Pro Ser Ser Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
                180                 185                 190

Asn Asn Tyr Lys Thr Thr Pro Pro Val Leu Asp Ser Asp Gly Ser Phe
                195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 4
<211> LENGTH: 348
<212> TYPE: PRT
<213> ORGANISM: artificial sequence
<220> FEATURE:
<221> NAME/KEY: source
<223> OTHER INFORMATION: /note=description of artificial sequence: this
      is a fusion protein sequence containing a portion of a human TACI
      receptor and a portion of a human immunoglobulin heavy chain
      sequence.

<400> SEQUENCE: 4

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
                20                  25                  30

Phe Arg Arg Ala Met Arg Ser Cys Pro Glu Glu Gln Tyr Trp Asp Pro
            35                  40                  45

Leu Leu Gly Thr Cys Met Ser Cys Lys Thr Ile Cys Asn His Gln Ser
50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
                100                 105                 110

Lys Leu Arg Ser Glu Pro Lys Ser Ser Asp Lys Thr His Thr Cys Pro
            115                 120                 125

Pro Cys Pro Ala Pro Glu Ala Glu Gly Ala Pro Ser Val Phe Leu Phe
130                 135                 140

```
Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
                260                 265                 270

Phe Tyr Pro Ser Asp Ile Ala Val Glu Trp Glu Ser Asn Gly Gln Pro
            275                 280                 285

Glu Asn Asn Tyr Lys Thr Thr Pro Pro Val Leu Asp Ser Asp Gly Ser
        290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345

<210> SEQ ID NO 5
<211> LENGTH: 879
<212> TYPE: DNA
<213> ORGANISM: homo sapiens

<400> SEQUENCE: 5
atgagtggcc tgggccggag caggcgaggt ggccggagcc gtgtggacca ggaggagcgc      60
tttccacagg gcctgtggac gggggtggct atgagatcct gccccgaaga gcagtactgg     120
gatcctctgc tgggtacctg catgtcctgc aaaaccattt gcaaccatca gagccagcgc     180
acctgtgcag ccttctgcag gtcactcagc tgccgcaagg agcaaggcaa gttctatgac     240
catctcctga gggactgcat cagctgtgcc tccatctgtg acagcaccc taagcaatgt     300 gcatacttct gtgagaacaa gctcaggagc ccagtgaacc ttccaccaga gctcaggaga     360
cagcggagtg agaagttgaa aacaattca gacaactcgg aaggtaccca aggattggag     420
cacagaggct cagaagcaag tccagctctc ccggggctga agctgagtgc agatcaggtg     480
gccctggtct acagcacgct ggggctctgc ctgtgtgccg tcctctgctg cttcctggtg     540
gcggtggcct gcttcctcaa gaagagggg gatccctgct cctgccagcc ccgctcaagg     600
ccccgtcaaa gtccggccaa gtcttcccag gatcacgcga tggaagccgg cagccctgtg     660
agcacatccc ccgagccagt ggagacctgc agcttctgct ccctgagtg cagggcgccc     720 acgcaggaga gcgcagtcac gcctgggacc ccgacccca cttgtgctgg aaggtggggg     780
tgccacacca ggaccacagt cctgcagcct tgcccacaca tcccagacag tggccttggc     840
attgtgtgtg tgcctgccca ggagggggc ccaggtgca                            879

<210> SEQ ID NO 6
<211> LENGTH: 753
```

```
<212> TYPE: DNA
<213> ORGANISM: artificial sequence
<220> FEATURE:
<221> NAME/KEY: source
<223> OTHER INFORMATION: /note=description of artificial sequence: DNA
      encoding SEQ ID NO:3

<400> SEQUENCE: 6
atgaagcacc tgtggttctt cctcctgctg gtggcggctc ccagatgggt cctgtccgag      60
cccaaatctt cagacaaaac tcacacatgc ccaccgtgcc cagcacctga agccaggggg     120
gcaccgtcag tcttcctctt ccccccaaaa cccaaggaca ccctcatgat ctcccggacc     180
cctgaggtca catgcgtggt ggtggacgtg agccacgaag accctgaggt caagttcaac     240
tggtacgtgg acggcgtgga ggtgcataat gccaagacaa agccgcggga ggagcagtac     300
aacagcacgt accgtgtggt cagcgtcctc accgtcctgc accaggactg gctgaatggc     360
aaggagtaca agtgcaaggt ctccaacaaa gccctcccat cctccatcga gaaaaccatc     420
tccaaagcca aagggcagcc ccgagaacca caggtgtaca ccctgccccc atcccgggat     480
gagctgacca agaaccaggt cagcctgacc tgcctggtca aaggcttcta tcccagcgac     540
atcgccgtgg agtgggagag caatgggcag ccggagaaca actacaagac cacgcctccc     600
gtgctggact ccgacggctc cttcttcctc tacagcaagc tcaccgtgga caagagcagg     660
tggcagcagg ggaacgtctt ctcatgctcc gtgatgcatg aggctctgca caaccactac     720
acgcagaaga gcctctccct gtctccgggt aaa                                  753

<210> SEQ ID NO 7
<211> LENGTH: 1044
<212> TYPE: DNA
<213> ORGANISM: artificial sequence
<220> FEATURE:
<221> NAME/KEY: source
<223> OTHER INFORMATION: /note=description of artificial sequence: DNA
      encoding the protein of SEQ ID NO: 4

<400> SEQUENCE: 7
atggatgcaa tgaagagagg gctctgctgt gtgctgctgc tgtgtggcgc cgtcttcgtt      60
tcgctcagcc aggaaatcca tgccgagttg agacgcttcc gtagagctat gagatcctgc     120
cccgaagagc agtactggga tcctctgctg gtacctgca tgtcctgcaa aaccatttgc      180
aaccatcaga gccagcgcac ctgtgcagcc ttctgcaggt cactcagctg ccgcaaggag     240
caaggcaagt tctatgacca tctcctgagg gactgcatca gctgtgcctc catctgtgga     300
cagcacccta gcaatgtgca atacttctgt gagaacaagc tcaggagcga gcccaaatct     360
tcagacaaaa ctcacacatg cccaccgtgc cagcacctg aagccagggg ggcaccgtca     420
gtcttcctct tccccccaaa acccaaggac accctcatga tctcccggac ccctgaggtc     480
acatgcgtgg tggtggacgt gagccacgaa gaccctgagg tcaagttcaa ctggtacgtg     540
gacggcgtgg aggtgcataa tgccaagaca agccgcggg aggagcagta caacagcacg     600
taccgtgtgg tcagcgtcct caccgtcctg caccaggact ggctgaatgg caaggagtac     660
aagtgcaagg tctccaacaa agccctccca tcctccatcg agaaaaccat ctccaaagcc     720
aaagggcagc ccgagaacc acaggtgtac accctgcccc catcccggga tgagctgacc     780
aagaaccagg tcagcctgac ctgcctggtc aaaggcttct atcccagcga catcgccgtg     840
gagtgggaga gcaatgggca gccggagaac aactacaaga ccacgcctcc cgtgctggac     900
tccgacggct ccttcttcct ctacagcaag ctcaccgtgg acaagagcag gtggcagcag     960
```

```
gggaacgtct tctcatgctc cgtgatgcat gaggctctgc acaaccacta cacgcagaag    1020
agcctctccc tgtctccggg taaa                                            1044
```

PROCESS FOR THE PURIFICATION OF FC-CONTAINING PROTEINS

CROSS REFERENCE TO RELATED APPLICATIONS

This application is the National Stage of International Application Number PCT/EP2007/058887, filed Aug. 27, 2007, which claims the benefit of European Application No. 06119611.9, filed Aug. 28, 2006 and U.S. Provisional Application No. 60/842,542, filed Sep. 6, 2006.

FIELD OF THE INVENTION

The present invention is in the field of protein purification. More specifically, it relates to the purification of an Fc-containing protein via cation exchange chromatography, in particular for reduction of the amount of free Fc-moieties in an Fc-containing protein preparation.

BACKGROUND OF THE INVENTION

Proteins have become commercially important as drugs that are generally called "biologicals". One of the greatest challenges is the development of cost effective and efficient processes for purification of proteins on a commercial scale. While many methods are now available for large-scale production of proteins, crude products, such as cell culture supernatants, contain not only the desired product but also impurities, which are difficult to separate from the desired product. Although cell culture supernatants of cells expressing recombinant protein products may contain less impurities if the cells are grown in serum-free medium, the host cell proteins (HCPs) still remain to be eliminated during the purification process. Additionally, the health authorities request high standards of purity for proteins intended for human administration.

A number of chromatographic systems are known that are widely used for protein purification.

Ion exchange chromatography systems are used for separation of proteins primarily on the basis of differences in charge.

Anion exchangers can be classified as either weak or strong. The charge group on a weak anion exchanger is a weak base, which becomes de-protonated and, therefore, loses its charge at high pH. DEAE-sepharose is an example of a weak anion exchanger, where the amino group can be positively charged below pH ~9 and gradually loses its charge at higher pH values. Diethylaminoethyl (DEAE) or diethyl-(2-hydroxy-propyl)aminoethyl (QAE) have chloride as counter ion, for instance. A strong anion exchanger, on the other hand, contains a strong base, which remains positively charged throughout the pH range normally used for ion exchange chromatography (pH 1-14). Q-sepharose (Q stands for quaternary ammonium) is an example for a strong anion exchanger.

Cation exchangers can also be classified as either weak or strong. A strong cation exchanger contains a strong acid (such as a sulfopropyl group) that remains charged from pH 1-14; whereas a weak cation exchanger contains a weak acid (such as a carboxymethyl group), which gradually loses its charge as the pH decreases below 4 or 5. Carboxymethyl (CM) and sulphopropyl (SP) have sodium as counter ion, for example.

A different chromatography resin is based on an insoluble hydroxylated calcium phosphate matrix called hydroxyapatite. Hydroxyapatite chromatography is a method of purifying proteins that utilizes an insoluble hydroxylated calcium phosphate $(Ca_5(PO_4)_3OH)_2$, which forms both the matrix and ligand. Functional groups consist of pairs of positively charged calcium ions (C-sites) and clusters of negatively charged phosphate groups (P-sites). The interactions between hydroxyapatite and proteins are complex and multi-mode. In one method of interaction, positively charged amino groups on proteins associate with the negatively charged P-sites and protein carboxyl groups interact by coordination complexation to C-sites (Shepard et al., 2000).

Crystalline hydroxyapatite was the first type of hydroxyapatite used in chromatography. Ceramic Hydroxyapatite (CHA) chromatography is a further development in hydroxyapatite chromatography. Ceramic hydroxyapatite has high durability, good protein binding capacity, and can be used at higher flow rates and pressures than crystalline hydroxyapatite. (Vola et al., 1993).

Hydroxyapatite has been used in the chromatographic separation of proteins, nucleic acids, as well as antibodies. In hydroxyapatite chromatography, the column is normally equilibrated, and the sample applied, in a low concentration of phosphate buffer and the adsorbed proteins are then eluted in a concentration gradient of phosphate buffer (Giovannini et al., 2000).

Yet a further way of purifying proteins is based on the affinity of a protein of interest to another protein that is immobilized to a chromatography resin. Examples for such immobilized ligands are the bacterial cell wall proteins Protein A and Protein G, having specificity to the Fc portion of certain immunoglobulins. Although both Protein A and Protein G have a strong affinity for IgG antibodies, they have varying affinities to other immunoglobulin classes and isotypes as well.

Protein A is a 43,000 Dalton protein that is produced by the bacteria *Staphylcoccus aureus* and contains four binding sites to the Fc regions of IgG. Protein G is produced from group G Streptococci and has two binding sites for the IgG Fc region. Both proteins have been widely characterized for their affinity to various types of immunoglobulins. Another development is Protein A/G, a genetically engineered protein that combines the binding capacities of Protein A and G. Protein L is a further bacterial protein, originating from Peptostreptococcus, binding to Immunoglobulins and fragments thereof containing Ig light chains (Akerstrom and Bjork, 1989).

Protein A, Protein G, and Protein L affinity chromatography are widely used for isolation and purification of antibodies.

Since the binding sites for Protein A and Protein G reside in the Fc region of an immunoglobulin, Protein A and Protein G (or Protein A/G) affinity chromatography also allows purification of so-called Fc-fusion proteins. Protein L binds to Ig light chains and can thus be used for the purification of light chain containing antibodies.

Antibodies, or immunoglobulins (Igs) consist of light chains and heavy chains linked together by disulphide bonds. The first domain located at the amino terminus of each chain is variable in amino acid sequence, providing the vast spectrum of antibody binding specificities. These domains are known as variable heavy (VH) and variable light (L) regions. The other domains of each chain are relatively invariant in amino acid sequence and are known as constant heavy (CH) and constant light (CL) regions.

The major classes of antibodies are IgA, IgD, IgE, IgG and IgM; and these classes may be further divided into subclasses (isotypes). For example, the IgG class has four subclasses, namely, $IgG_1$, $IgG_2$, $IgG_3$, and $IgG_4$.

The differences between antibody classes are derived from differences in the heavy chain constant regions, containing between 1 and 4 constant domains (CH1—CH4), depending on the immunoglobulin class. A so-called hinge region is located between the CH1 and CH2 domains. The hinge region is particularly sensitive to proteolytic cleavage; such proteolysis yields two or three fragments depending on the precise site of cleavage. The part of the heavy chain constant region containing the CH2 and CH3 domains is also called the "Fc" part of the immunoglobulin. Antibodies are thus Fc-containing proteins. Another type of Fc-containing proteins are the so-called Fc-fusion proteins.

Several antibodies that are used as therapeutic proteins are known. Examples for recombinant antibodies on the market are for instance: Abciximab, Rituximab, Basiliximab, Daclizumab, Palivizumab, Infliximab, Trastuzumab, Alemtuzumab, Adalimumab, Cetuximab, Efalizumab, Ibritumomab, Bevacizumab, or Omalizumab. Fc-fusion proteins are chimeric proteins consisting of the effector region of a protein, such as the Fab region of an antibody or the binding region of a receptor, fused to the Fc region of an immunoglobulin that is frequently an immunoglobulin G (IgG). Fc-fusion proteins are widely used as therapeutics as they offer advantages conferred by the Fc region, such as:

The possibility of purification using protein A or protein G affinity chromatography with affinities varying according to the IgG isotype. Human $IgG_1$, $IgG_2$ and $IgG_4$ bind strongly to Protein A and all human IgGs including $IgG_3$ bind strongly to Protein G;

An increased half-life in the circulatory system, since the Fc region binds to the salvage receptor FcRn which protects from lysosomal degradation;

Depending on the medical use of the Fc-fusion protein, the Fc effector functions may be desirable. Such effector functions include antibody-dependent cellular cytotoxicity (ADCC) through interactions with Fc receptors (FcγR5) and complement-dependent cytotoxicity (CDC) by binding to the complement component 1q (C1q). IgG isoforms exert different levels of effector functions. Human $IgG_1$ and $IgG_3$ have strong ADCC and CDC effects while human $IgG_2$ exerts weak ADCC and CDC effects. Human $IgG_4$ displays weak ADCC and no CDC effects.

Serum half-life and effector functions can be modulated by engineering the Fc region to increase or reduce its binding to FcRn, FcγR5 and C1q respectively, depending on the therapeutic use intended for the Fc-fusion protein.

In ADCC, the Fc region of an antibody binds to Fc receptors (FcγRs) on the surface of immune effector cells such as natural killers and macrophages, leading to the phagocytosis or lysis of the targeted cells.

In CDC, the antibodies kill the targeted cells by triggering the complement cascade at the cell surface. IgG isoforms exert different levels of effector functions increasing in the order of $IgG_4 < IgG_2 < IgG_1 \leq IgG_3$. Human $IgG_1$ displays high ADCC and CDC, and is the most suitable for therapeutic use against pathogens and cancer cells.

Under certain circumstances, for example when depletion of the target cell is undesirable, abrogating or diminishing effector functions may be required. On the contrary, in the case of antibodies intended for oncology use, increasing effector functions may improve their therapeutic activity (Carter et al., 2006).

Modifying effector functions can be achieved by engineering the Fc region to either improve or reduce binding of FcγRs or the complement factors.

The binding of IgG to the activating (FcγRI, FcγRIIa, FcγRIIIa and FcγRIIIb) and inhibitory (FcγRIIb) FcγRs or the first component of complement (C1q) depends on residues located in the hinge region and the CH2 domain. Two regions of the CH2 domain are critical for FcγRs and complement C1q binding, and have unique sequences in $IgG_2$ and $IgG_4$. For instance, substitution of $IgG_2$ residues at positions 233-236 into human IgG1 greatly reduced ADCC and CDC (Armour et al., 1999 and Shields et al., 2001).

Numerous mutations have been made in the CH2 domain of IgG and their effect on ADCC and CDC was tested in vitro (Shields et al., 2001, Idusogie et al., 2001 and 2000, Steurer et al., 1995). In particular, a mutation to alanine at E333 was reported to increase both ADCC and CDC (Idusogie et al., 2001 and 2000).

Increasing the serum half-life of a therapeutic antibody is another way to improve its efficacy, allowing higher circulating levels, less frequent administration and reduced doses. This can be achieved by enhancing the binding of the Fc region to neonatal FcR (FcRn). FcRn, which is expressed on the surface of endothelial cells, binds the IgG in a pH-dependent manner and protects it from degradation. Several mutations located at the interface between the CH2 and CH3 domains have been shown to increase the half-life of $IgG_1$ (Hinton et al., 2004 and Vaccaro et al., 2005).

The following Table 1 summarizes some known mutations of the IgG Fc-region (taken from Invivogen's website).

| Engineered Fc | IgG Isotype | Mutations | Properties | Potential Benefits | Applications |
| --- | --- | --- | --- | --- | --- |
| hIgG1e1 | human IgG1 | T250Q/M428L | Increased plasma half-life | Improved localization to target; increased efficacy; reduced dose or frequency of administration | Vaccination; therapeutic use |
| hIgG1e2 | human IgG1 | M252Y/S254T/T256E + H433K/N434F | Increased plasma half-life | Improved localization to target; increased efficacy; reduced dose or frequency of administration | Vaccination; therapeutic us |
| hIgG1e3 | human IgG1 | E233P/L234V/L235A/ ΔG236 + A327G/A330S/P331S | Reduced ADCC and CDC | Reduced adverse events | Therapeutic use without cell depletion |
| hIgG1e4 | human IgG1 | E333A | Increased ADCC and CDC | Increased efficacy | Therapeutic use with cell depletion |
| hIgG2e1 | human IgG2 | K322A | Reduced CDC | Reduced adverse events | Vaccination; therapeutic use |

A class of Fc-fusion proteins having therapeutic utility, Fc-regions have been fused to extracellular domains of certain receptors belonging to the tumor necrosis factor receptor (TNF-R) superfamily (Locksley et al., 2001, Bodmer et al., 2002, Bossen et al., 2006). A hallmark of the members of the TNFR family is the presence of cysteine-rich pseudo-repeats in the extracellular domain, as described e.g. by Naismith and Sprang, 1998.

The two TNF receptors, p55 (TNFR1) and p75 TNFR (TNFR2) are examples of such members of the TNFR superfamily. Etanercept is an Fc-fusion protein containing the soluble part of the p75 TNFR (e.g. WO91/03553, WO 94/06476). Under the trade name Enbrel®, it is marketed for treatment of Endometriosis, Hepatitis C virus infection, HIV infection, Psoriatic arthritis, Psoriasis, Rheumatoid arthritis, Asthma, Ankylosing spondylitis, Cardiac failure, Graft versus host disease, Pulmonary fibrosis, Crohns disease. Lenercept is a fusion protein containing extracellular components of human p55 TNF receptor and the Fc portion of human IgG, and is intended for the potential treatment of severe sepsis and multiple sclerosis.

OX40 is also a member of the TNFR superfamily. OX40-IgG1 and OX40-hIG4mut fusion proteins have been prepared for treatment of inflammatory and autoimmune diseases such as Crohn's Disease.

An Fc-fusion protein of the BAFF-R, also called BR3, designated BR3-Fc, is a soluble decoy receptor from a series of inhibitors of BAFF (B-cell activating factor of the TNF family), is being developed for the potential treatment of autoimmune diseases such as rheumatoid arthritis (RA) and systemic lupus erythematosus (SLE).

BCMA is a further receptor belonging to the TNFR superfamily. A BCMA-Ig fusion protein has been described to inhibit autoimmune disease (Melchers, 2006).

Another receptor of the TNF-R superfamily is TACI, the transmembrane activator and CAML-interactor (von Bülow and Bram, 1997; U.S. Pat. No. 5,969,102, Gross et al., 2000), which has an extracellular domain containing two cysteine-rich pseudo-repeats. TACI binds two members of the tumor necrosis factor (TNF) ligand family. One ligand is designated BLyS, BAFF, neutrokine-α, TALL-1, zTNF4, or THANK (Moore et al., 1999). The other ligand has been designated as APRIL, TNRF death ligand-1 or ZTNF2 (Hahne et al., J. Exp. Med. 188: 1185 (1998).

Fusion proteins containing soluble forms of the TACI receptor fused to an IgG Fc region are known as well and were designated TACI-Fc (WO 00/40716, WO 02/094852). TACI-Fc inhibits the binding of BLyS and APRIL to B-cells (Xia et al., 2000). It is being developed for the treatment of autoimmune diseases, including systemic lupus erythematosus (SLE), rheumatoid arthritis (RA) and hematological malignancies, as well as for treatment of multiple sclerosis (MS). In addition to this, TACI-Fc is being developed in multiple myeloma (MM) (Novak et al., 2004; Moreau et al., 2004) and non-Hodgkin's lymphoma (NHL), chronic lymphocytic leukemia (CLL) and Waldenstrom's macroglobulemia (WM).

Given the therapeutic utility of Fc-containing proteins, particularly antibodies and Fc-fusion proteins, there is a need for significant amounts of highly purified protein that is adequate for human administration.

SUMMARY OF THE INVENTION

One of the problems that may be encountered during production of Fc-containing proteins is the presence of "free Fc-moieties", i.e. polypeptide fragments derived from the Fc-containing protein, which does not contain a substantial portion derived from an antibody variable region or from another specific protein or domain normally present in the Fc-fusion protein.

The present invention addresses this problem. It is based on the development of a purification process for a fluid, composition or preparation of an Fc-containing protein, by which the amount of free Fc-moieties that may be present as an impurity can be reduced.

Therefore the invention relates to a method for reducing the concentration of free Fc-moieties in a fluid comprising an Fc-containing protein, the method comprising subjecting said fluid to cation exchange chromatography.

In a second aspect, the invention relates to the use of cation exchange chromatography for the reduction of free Fc in an Fc-containing protein preparation.

In a third aspect, the invention relates to a purified Fc-containing protein, comprising less than 5% or less than 2% or less than 1% or less than 0.5% or less than 0.2% or less than 0.1% of free Fc-moieties.

BRIEF DESCRIPTION OF THE SEQUENCE LISTING

Figure 1:
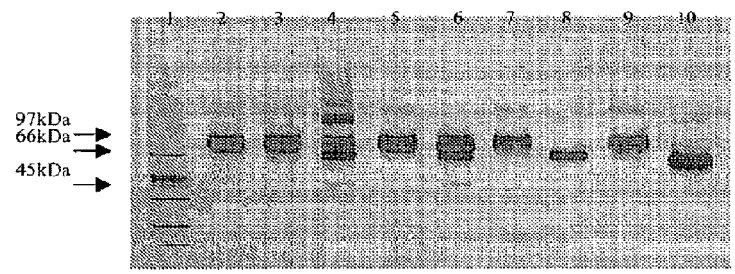
FIG. 1 shows a non-reduced silver stained SDS-PAGE of different fractions stemming from the cation exchange chromatography described in Example 2. Lane 1: Molecular weight markers, Lane 2: purified TACI-Fc, Lane 3: load, Lane 4: wash 2, Lane 5: eluate 2, Lane 6: wash 3, Lane 7: eluate 3, Lane 8: wash 1, Lane 9: eluate 1, Lane 10: purified free Fc.

SEQ ID NO: 1 is a Cysteine fingerprint sequence (cysteine rich pseudo repeat) common to members of the TNFR superfamily;

SEQ ID NO: 2 is the full length sequence of the human TACI receptor (e.g. described in WO 98/39361);

SEQ ID NO: 3 is an example of a human Fc sequence of the invention (e.g. described in WO 02/094852);

SEQ ID NO: 4 is a preferred Fc-fusion protein of the invention, comprising sequences derived from the extracellular portion of TACI and a human IgG, Fc portion (e.g. described in WO 02/094852);

SEQ ID NO: 5 is a polynucleotide coding for a polypeptide of SEQ ID NO: 2;

SEQ ID NO: 6 is a polynucleotide coding for a polypeptide of SEQ ID NO: 3;

SEQ ID NO: 7 is a polynucleotide coding for a polypeptide of SEQ ID NO: 4.

DETAILED DESCRIPTION OF THE INVENTION

The present invention is based on the finding that cation exchange chromatography can reduce the amount or extent of free Fc-moieties that may be present in a fluid or composition of an Fc-containing protein.

The invention therefore relates to a method for reducing the concentration of free Fc-moieties in a fluid comprising an Fc-containing protein, the method comprising subjecting said fluid to cation exchange chromatography.

The fluid comprising the Fc-containing protein may be any composition or preparation, such as e.g. a body fluid derived from a human or animal, or a fluid derived from a cell culture, such as e.g. a cell culture supernatant. It may also be a fluid derived from another purification step, such as e.g. the eluate or flow-through from a capture step or any other suitable purification step such as the ones explained in more detail below.

The term "Fc-containing protein", as used herein, refers to any protein having at least one immunoglobulin constant domain selected from the CH1, hinge, CH2, CH3, CH4 domain, or any combination thereof, and preferably a hinge, CH2 and CH3 domain. The immunoglobulin constant domain may be derived from any of IgG, IgA, IgE, IgM, or combination or isotype thereof. Preferably, it is IgG, such as e.g. $IgG_1$, $IgG_2$, $IgG_3$ or $IgG_4$. More preferably, it is $IgG_1$.

An Fc-containing protein, in accordance with the present invention, may thus be e.g. an antibody or an Fc-fusion protein, or variants thereof, such as fragments, muteins or functional derivatives of antibodies or Fc-fusion proteins.

The Fc-containing protein of the invention may be a monomer, dimer or multimer. The Fc-containing protein may also be a "pseudo-dimer" (sometimes called "monomer"), containing a dimeric Fc-moiety (e.g. a dimer of two disulfide-bridged hinge-CH2-CH3 constructs), of which only one is fused to a further moiety such as an immunoglobulin variable domain, a ligand binding and optionally inhibiting fragment of a receptor, or any other protein. An example for such a pseudo-dimer is an Fc-fusion protein having Interferon-β fused to one of the two IgG hinge-CH2-CH3 constructs such as e.g. the one described in WO 2005/001025.

The Fc-containing protein may also be a heterodimer, containing two different non-immunoglobulin portions or immunoglobulin variable domains, or a homodimer, containing two copies of a single non-immunoglobulin portion or immunoglobulin variable domain.

Preferably, the Fc-containing protein is a dimer. It is also preferred that the Fc-containing protein of the invention is a homo-dimer.

In accordance with the present invention, the Fc-moiety of the Fc-containing protein may also be modified in order to modulate effector functions.

For instance, the following Fc mutations, according to EU index positions (Kabat et al., 1991), can be introduced if the Fc-moiety is derived from $IgG_1$:

T250Q/M428L
M252Y/S254T/T256E+H433K/N434F
E233P/L234V/L235A/ΔG236+A327 G/A330S/P331S
E333A; K322A.

Further Fc mutations may e.g. be the substitutions at EU index positions selected from 330, 331 234, or 235, or combinations thereof. An amino acid substitution at EU index position 297 located in the CH2 domain may also be introduced into the Fc-moiety in the context of the present invention, eliminating a potential site of N-linked carbohydrate attachment. Furthermore, the cysteine residue at EU index position 220 may also be replaced with a serine residue, eliminating the cysteine residue that normally forms disulfide bonds with the immunoglobulin light chain constant region.

In accordance with the present invention, it is preferred that the Fc-moiety comprises or consists of SEQ ID NO: 3 or is encoded by a polynucleotide comprising or consisting of SEQ ID NO: 6.

In a preferred embodiment, the Fc-containing protein comprises an immunoglobulin variable region, e.g. one or more heavy chain variable domains and/or one or more light chain variable domains. Preferably, the antibody contains one or two heavy chain variable domains. More preferably, the antibody additionally contains one or two light chain constant and/or variable domains.

It is preferred that the Fc-containing protein is an antibody.

The term "antibody" refers to an immunoglobulin or fragment thereof, and encompasses any polypeptide comprising an antigen-binding site. The term includes, but is not limited to, polyclonal, monoclonal, monospecific, polyspecific, non-specific, humanized, human, chimeric, single-chain, synthetic, recombinant, hybrid, mutated, grafted, or in vitro generated antibodies. The antibody may be selected from any of the known antibody isotypes, for example, IgA, IgG, IgD, IgE, IgM. The antibody may be a monomer, dimer, or multimer such as a trimer, or pentamer.

Examples of antibodies that can be purified in accordance with the present invention are Abciximab, Rituximab, Basiliximab, Daclizumab, Palivizumab, Infliximab, Trastuzumab, Alemtuzumab, Adalimumab, Cetuximab, Efalizumab, Ibritumomab, Bevacizumab, or Omalizumab. Further examples of antibodies that can be subjected to cation exchange chromatography in accordance with the present invention are antibodies directed against:

CD2, CD3, CD4, CD8, CD11a, CD11b, CD14, CD18, CD20, CD22, CD23, CD25, CD33, CD40, CD44, CD52, CD80, CD86, CD147, CD164, IL-2 receptor, IL-4 receptor, IL-6 receptor, IL-12 receptor, IL-18 receptor subunits (IL-18R-alpha, IL-18R-beta), TACI, BCMA, BAFF-R, EGF receptor, VEGF receptor, integrin a4p7, the integrin VLA4, B2 integrins, TRAIL receptors 1, 2, 3, and 4, RANK, RANK ligand, epithelial cell adhesion molecule (EpCAM), intercellular adhesion molecule-3 (ICAM-3), CTLA4, Fc-gamma-I, II or III receptor, HLA-DR 10 beta, HLA-DR antigen, or L-selectin.

Antibodies directed against TNF, Blys, or Interferon-γ are further examples of therapeutically interesting antibodies.

Fc-fusion proteins are also Fc-containing proteins that are preferably subjected to the method of the invention.

The term "Fc-fusion protein", as used herein, is meant to encompass proteins, in particular therapeutic proteins, comprising an immunoglobulin-derived moiety, which will be called herein the "Fc-moiety", and a moiety derived from a second, non-immunoglobulin protein, which will be called herein the "therapeutic moiety", irrespective of whether or not treatment of disease is intended.

Therapeutic Fc-fusion proteins, i.e. Fc-fusion proteins intended for treatment or prevention of disease of an animal or preferably for human treatment or administration, are especially suitable to be purified in accordance with the invention.

Any Fc-fusion protein may be purified in accordance with the present invention, such as e.g. an Interferon-β-containing fusion protein. Preferably, the method of the invention is for purifying an Fc-fusion protein comprising a ligand binding fragment, such as all or part of an extracellular domain, of a member of the tumor necrosis factor receptor (TNFR) superfamily.

The therapeutic moiety of an Fc-fusion protein may e.g. be or be derived from EPO, TPO, Growth Hormone, Interferon-alpha, Interferon-beta, Interferon-gamma, PDGF-beta, VEGF, IL-1alpha, IL-1beta, IL-2, IL-4, IL-5, IL-8, IL-10, IL-12, IL-18, IL-18 binding protein, TGF-beta, TNF-alpha, or TNF-beta.

The therapeutic moiety of an Fc-fusion protein may also be derived from a receptor, e.g a transmembrane receptor, preferably be or be derived from the extracellular domain of a receptor, and in particular a ligand binding fragment of the extracellular part or domain of a given receptor. Examples for therapeutically interesting receptors are CD2, CD3, CD4, CD8, CD11a, CD11b, CD14, CD18, CD20, CD22, CD23, CD25, CD33, CD40, CD44, CD52, CD80, CD86, CD147, CD164, IL-2 receptor, IL-4 receptor, IL-6 receptor, IL-12 receptor, IL-18 receptor subunits (IL-18R-alpha, IL-18R- beta), EGF receptor, VEGF receptor, integrin alpha 4 10 beta 7, the integrin VLA4, B2 integrins, TRAIL receptors 1, 2, 3, and 4, RANK, RANK ligand, epithelial cell adhesion molecule (EpCAM), intercellular adhesion molecule-3 (ICAM-3), CTLA4 (which is a cytotoxic T lymphocyte-associated antigen), Fc-gamma-1, II or III receptor, HLA-DR 10 beta, HLA-DR antigen, L-selectin.

It is highly preferred that the therapeutic moiety is derived from a receptor belonging to the TNFR superfamily. The therapeutic moiety may e.g. be or be derived from the extracellular domain of TNFR1 (p55), TNFR2 (p75), OX40, Osteoprotegerin, CD27, CD30, CD40, RANK, DR3, Fas ligand, TRAIL-R1, TRAIL-R2, TRAIL-R3, TAIL-R4, NGFR, AITR, BAFFR, BCMA, TACI.

In accordance with the present invention, the therapeutic moiety derived from a member of the TNFR superfamily preferably comprises or consists of all or part of the extracellular domain of the member of the TNFR, and more preferably comprises a ligand binding fragment of such a member of the TNFR.

The following Table 5 lists members of the TNFR superfamily from which a therapeutic moiety in accordance with the present invention may be derived, and their respective ligands. A "ligand binding fragment" of a member of the TNFR family can easily be determined by the person skilled in the art, e.g. in a simple in vitro assay measuring binding between protein fragment of a given receptor and the respective ligand. Such an assay can e.g. be a simple in vitro RIA- or ELISA-type sandwich assay wherein one of the proteins, e.g. the receptor fragment, is immobilized to a carrier (e.g. an ELISA plate) and is incubated, following appropriate blocking of the protein binding sites on the carrier, with the second protein, e.g. the ligand. After incubation, ligand binding is detected e.g. by way of radioactive labeling of the ligand and determination of the bound radioactivity, after appropriate washing, in a scintillation counter. Binding of the ligand can also be determined with a labeled antibody, or a first ligand-specific antibody and a second, labeled antibody directed against the constant part of the first antibody. Ligand binding can thus be easily determined, depending of the label used, e.g. in a color reaction.

Preferably, the method of the present invention is for purifying an Fc-fusion protein comprising a therapeutic moiety derived from a member of the TNFR superfamily selected from those listed in Table 5.

TABLE 5

The TNFR superfamily (according to Locksley et al., 2001 and Bossen et al., 2006)

| Member of TNFR superfamily | Ligand |
| --- | --- |
| NGFR | NGF |
| EDAR | EDA-A1 |
| XEDAR | EDA-A2 |
| CD40 | CD40L |
| Fas | FasL |
| Ox40 | OX40L |
| AITR | AITRL |
| GITR | GITRL |
| CD30 | CD30L |
| CD40 | CD40L |
| HveA | LIGHT, LT-alpha |
| 4-1BB | 4-1BBL |
| TNFR2 | TNF-alpha, LT-alpha, LT-alpha-beta |
| LT-betaR | LIGHT, LT-alpha, LT-alpha-beta |
| DR3 | TL1A |
| CD27 | CD27L |
| TNFR1 | TNF-alpha, LT-alpha, LT-alpha-beta |

TABLE 5-continued

The TNFR superfamily (according to Locksley et al., 2001 and Bossen et al., 2006)

| Member of TNFR superfamily | Ligand |
| --- | --- |
| LTBR | LT-beta |
| RANK | RANKL |
| TACI | BlyS, APRIL |
| BCMA | BlyS, APRIL |
| BAFF-R | BAFF (=BlyS) |
| TRAILR1 | TRAIL |
| TRAILR2 | TRAIL |
| TRAILR3 | TRAIL |
| TRAILR4 | TRAIL |
| Fn14 | TWEAK |
| OPG | RANKL, TRAIL |
| DR4 | TRAIL |
| DR5 | TRAIL |
| DcR1 | TRAIL |
| DcR2 | TRAIL |
| DcR3 | FasL, LIGHT, TL1A |

In a preferred embodiment, the Fc-fusion protein comprises a therapeutic moiety selected from an extracellular domain of TNFR1, TNFR2, or a TNF binding fragment thereof.

In a further preferred embodiment, the Fc-fusion protein comprises a therapeutic moiety selected from an extracellular domain of BAFF—R, BCMA, or TACI, or a fragment thereof binding at least one of Blys or APRIL.

An assay for testing the capability of binding to Blys or APRIL is described e.g. in Hymowitz et al., 2006.

In yet a further preferred embodiment, the therapeutic moiety of an Fc-fusion protein comprises the Cysteine rich pseudo-repeat of SEQ ID NO: 1.

If is further preferred that the therapeutic moiety is derived from TACI. TACI is preferably human TACI. SEQ ID NO: 2, which corresponds to the amino acid sequence of human full-length TACI receptor (also SwissProt entry 014836). More preferably, the therapeutic moiety comprises a soluble portion of TACI, preferably derived from the extracellular domain of TACI. Preferably, the TACI-derived therapeutic moiety comprises at least amino acids 33 to 67 of SEQ ID NO: 2 and/or amino acids 70 to 104 of SEQ ID NO: 2. In a preferred embodiment, the TACI extracellular domain included in the therapeutic moiety according to the invention comprises or consist of amino acids 1 to 166 of SEQ ID NO: 2 or amino acids 30 to 166 of SEQ ID NO: 2, or amino acids 30 to 119 of SEQ ID NO: 2, or amino acids 30 to 110 of SEQ ID NO: 2. All of those therapeutic moieties are preferred for the preparation of the Fc-fusion protein to be purified by the method of the invention and are combined with the Fc-moieties described in detail above, and in particular with an Fc-moiety comprising or consisting of SEQ ID NO: 3. A highly preferred Fc-fusion protein to be purified in accordance with the present invention comprises or consists of SEQ ID NO: 4 or encoded by the polynucleotide of SEQ ID NO: 7.

Hence, it is highly preferred that the Fc-fusion protein comprises a polypeptide selected from
 a. amino acids 34 to 66 of SEQ ID NO: 2;
 b. amino acids 71 to 104 of SEQ ID NO: 2;
 c. amino acids 34 to 104 of SEQ ID NO: 2;
 d. amino acids 30 to 110 of SEQ ID NO: 2;
 e. SEQ ID NO: 3;
 f. SEQ ID NO: 4;
 g. a polypeptide encoded by a polynucleotide hybridizing to the complement of SEQ ID NO: 5 or 6 or 7 under highly stringent conditions; and h. a mutein of any of (c), (d), (e), or (f) having at least 80% or 85% or 90% or 95% sequence identity to the polypeptide of (c), (d), (e) or (f);

wherein the polypeptide binds to at least one of Blys or APRIL.

In accordance with the present invention, the Fc-containing protein is subjected to cation exchange chromatography in order to reduce, decrease, or eliminate free Fc-moieties, preferably at least by 50, 40, 30, 20 or 10% of the total protein concentration, or more preferably less than 10%.

The term "free EC moieties", "free Fc moiety", or simply "free Fc", as used herein, is meant to encompass any part of the Fc-containing protein to be purified in accordance with the present invention, which is derived from the immunoglobulin constant domain or domains without comprising complete further domains. Thus, if the Fc-containing protein comprises immunoglobulin variable domains, free Fc does not contain significant portions of the variable domains. If the Fc-containing protein is an Fc-fusion protein, free Fc does not contain significant portions of the therapeutic moiety of the Fc-fusion protein. Free Fc may e.g. contain dimers of the IgG hinge, CH2 and CH3 domains, which are not linked or bound to significant portions of a therapeutic moiety or immunoglobulin variable domains, such as e.g. the Fc part that is generated by papain cleavage. A "significant portion" may e.g. be no less than 80, 85, 90, 95, 98 or 99% of the full-length variable domain or therapeutic moiety present in the Fc-containing protein.

Monomers derived from the Fc-moiety may also be contained in the free Fc fraction. It is understood that free Fc may still contain a number of amino acid residues from the therapeutic moiety or the Ig variable domains, such as e.g. one to fifty or one to twenty, or one to ten, or one to five amino acids, or one or two single amino acids, belonging to the therapeutic moiety or variable domain, still fused to the Fc-moiety.

The cation exchange chromatography may be carried out on any suitable cation exchange resin, such as e.g. weak or strong cation exchangers as explained above in the Background of the Invention.

Preferably, the cation exchange chromatography is carried out on a strong cation exchange resin. More preferably, the cation exchange material comprises a cross-linked methacrylate modified with $SO_3^-$ groups. A column commercially available under the name Fractogel EMD $SO_3^-$ (from Merck) is an example of a cation exchange resin that is particularly suitable in the context of the present method.

Preferably, the fluid or composition comprising the Fc-containing protein is loaded to a cation exchange resin at a pH of at least one unit below the isoelectric point (pI) of said Fc-fusion protein.

In a preferred embodiment, the cation exchange resin is washed with a buffer having a conductivity of 6 to 10 mS/cm and at a pH of 5.5 to 7.5.

The buffer may e.g. have a conductivity at 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, or 9.9 mS/cm.

More preferably, the conductivity ranges from 7.6 to 9.2, i.e. 8.4±0.8 mS/cm. The washing step is preferably carried out at a pH ranging from 5.5 to 7.5, preferably from 6.0 to 7.0.

The pH of the buffer may e.g. be at 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5.

In a further preferred embodiment, the washing step is carried out in a buffer comprising 60 to 140, preferably 70 to 130, more preferably 75 to 125 mM sodium phosphate. The buffer may e.g. comprise 65, 70, 75, 80, 85, 90, 95, 100, 105, 110, 115, 120, 125, 130, 135, or 140 mM sodium phosphate.

In a further preferred embodiment, the cation exchange column is eluted at a pH ranging from 7.0 to 8.5, preferably 7.25 or 7.3 or 7.35 or 7.4 or 7.45 or 7.5 or 7.55 or 7.6 or 7.65 or 7.7 or 7.75 or 7.8 or 7.85 or 7.9 or 7.95 or 8.0 or 8.05 or 8.1 or 8.15 or 8.2 or 8.25 or 8.3 or 8.35 or 8.4 or 8.45 or 8.5.

Elution may preferably be carried out at a conductivity ranging from 15 to 22 mS/cm. For instance, the conductivity may be selected from 15, 16, 17, 18, 19, 20, 21, or 22 mS/cm.

A preferred buffer for elution is a phosphate buffer.

In accordance with the present invention, cation exchange chromatography can preferably be used for elimination or reduction of free Fc in the range of 5 to 15 fold. Thus, a reduction of the concentration of free Fc in the Fc-containing protein comprising fluid, preparation or composition to less than 20% or less than 15% or less than 10% or less than 5% or less than 2% or less than 1% or less than 0.8% or less than 0.5% or less than 0.3% or less than 0.2% or less than 0.1% of the total protein concentration can be achieved.

In a preferred embodiment, the cation exchange chromatography may be used in a purification method having one or more additional steps, preferably selected from affinity chromatography, anion exchange chromatography and hydroxyapatite chromatography.

In a highly preferred embodiment, the method of the invention is used as a second step of a purification scheme of an Fc-containing protein comprising the following steps:

a. Subjecting a fluid comprising said Fc-containing protein to Protein A or Protein G or Protein L affinity chromatography;

b. Subjecting the eluate of step (a) to Cation exchange chromatography;

c. Subjecting the eluate of step (b) to Anion exchange chromatography;

d. Subjecting the flow-through of step (c) to Hydroxyapatite chromatography and collecting the eluate to obtain purified Fc-containing protein.

In accordance with the present invention, a fluid comprising an Fc-containing protein is first subjected to Protein A or Protein G or Protein L or Protein A/G affinity chromatography. The fluid may preferably be cell culture material, e.g. solubilized cells, more preferably cell culture supernatant. The term "cell culture supernatant", as used herein, refers to a medium in which cells are cultured and into which proteins are secreted provided they contain appropriate cellular signals, so-called signal peptides. It is preferred that the Fc-containing protein expressing cells are cultured under serum-free culture conditions. Thus, preferably, the cell culture supernatant is devoid of animal-serum derived components. Most preferably, the cell culture medium is a chemically defined medium.

The Protein A, G, A/G or L used for the affinity chromatography may e.g. be recombinant. It may also be modified in order to improve its properties (such as e.g. in the resin called MabSelect SuRe, commercially available from GE Healthcare). In a preferred embodiment, step (a) is carried out on a resin comprising cross-linked agarose modified with recombinant Protein A. A column commercially available under the name Mabselect Xtra (from GE Healthcare) is an example of an affinity resin that is particularly suitable for step (a) of the present method.

The Protein A or G or L affinity chromatography is preferably used as a capture step, and thus serves for purification of the Fc-containing protein, in particular elimination of host cell proteins and Fc-containing protein aggregates, and for concentration of the Fc-containing protein preparation.

The term "aggregates", as used herein, is meant to refer to protein aggregates, and encompasses multimers (such as dimers, tetramers or higher order aggregates) of the Fc-containing protein to be purified and may result e.g. in high molecular weight aggregates.

The affinity chromatography has the further advantage of reducing aggregate levels by 2 to 4 fold.

In using the Protein A or G or A/G or L affinity chromatography, host cell protein levels may be reduced by 100 to 300 fold.

In a preferred embodiment of the invention, the elution in step (a) is carried out at a pH ranging from 2.8 to 4.5, preferably from 3.0 to 4.2, more preferably at 3.5, 3.55, 3.6, 3.65, 3.7, 3.75, 3.8, 3.85, 3.9, 3.95, 4.0, 4.05, 4.1, or 4, 15. The elution in step (a) may also be carried out with a pH gradient, preferably a gradient from pH 4.5 to 2.8.

In a further preferred embodiment, the elution in step (a) is carried out in a buffer selected from sodium acetate or sodium citrate. Suitable buffer concentrations are e.g. selected from 50 mM or 100 mM or 150 mM or 200 mM or 250 mM.

In accordance with the present invention, the eluate from the Protein A or Protein G or Protein A/G or Protein L chromatography is subjected to cation exchange chromatography, as explained in detail above.

Preferably, the eluate of the cation exchange chromatography, i.e. of step (b), is diluted or dialysed into an appropriate loading buffer before loading it on the anion exchange column. The anion exchange column is also preferably equilibrated with the loading buffer.

A preferred pH for the loading buffer is one unit below the pI. Suitable pH values range from 6.0 to 8.5, preferably from 7.0 to 8.0, e.g. 7.0, 7.05, 7.1, 7.15, 7.2, 7.25, 7.3, 7.35, 7.4, 7.45, 7.5, 7.55, 7, 6, 7.65, 7.7, 7.75, 7.8, 7.85, 7.9, 7.95, or 8.0. A preferred conductivity for the loading buffer is in the range of 3.0 to 4.6 mS/cm.

An appropriate equilibration/loading buffer may e.g. be sodium phosphate at a concentration ranging from 5 to 35, preferably from 20 to 30 mM. The buffer concentration may e.g. be at 10, 15, 20, 25, 30 mM. In the frame of the present invention, the flow-through (also called break-through) of the anion exchange chromatography, comprising the Fc-containing protein of interest, is being collected.

Step (c) of the method of the invention further reduces aggregates 3 to 5 fold and host cell proteins 30 to 70 fold.

In accordance with the present invention, the flow-through of the anion exchange chromatography of step (c) is then used for further purification by hydroxyapatite chromatography. Any hydroxyapatite resin may be used to carry out step (d) of the method according to the invention. In a preferred embodiment, step (d) is carried out on a ceramic hydroxyapatite resin, such as a type I or type II hydroxyapatite resin. The hydroxyapatite resin may have particles of any size such as 20, 40 or 80 p.m. In a highly preferred embodiment, the ceramic hydroxyapatite resin comprises particles having a size of 40 μm. A hydroxyapatite resin that is particularly suitable for step (d) of the present method is a column commercially available under the name CHT Ceramic Hydroxyapatite Type I, 40 μm.

In a preferred embodiment, the flow-through from step (c) is directly loaded on the hydroxyapatite resin, i.e. without previous dilution or dialysis into an appropriate loading buffer. Loading is preferably carried out at a pH of 6.5 to 7.5, such as 6.6, 6.7, 6.8, 6.9, 7.1, 7.2, 7.3, or 7.4, and preferably 7.0.

In a further preferred embodiment, the elution in step (d) is carried out in the presence of sodium phosphate ranging from 2 to 10 mM, preferably ranging from 2.75 to 5.25 mM, such as e.g. at 3, 3.25, 3.5, 3.75, 4, 4.25, 4, 5, 4.75, 5.

In yet a further preferred embodiment, the elution in step (d) is carried out at a pH ranging from 6.0 to 7.0, e.g. at 6.1, 6.2, 6.3, 6.4, 6.5, 6.6, 6.7, 6.8, 6.9.

In another preferred embodiment, elution in step (d) is carried out in the presence of potassium chloride ranging from 0.4 to 1 M, preferably at 0.45, 0.5, 0.55, 0.6, 0.65, 0.7, 0.75, 0.8, 0.85, 0.9, 0.95 M, most preferably at 0.6 M.

In accordance with the present invention, the eluate of the hydroxyapatite chromatography is collected, containing the finally purified Fc-containing protein preparation.

Suitable matrix materials, i.e. carrier materials for the chromatographic resins used in steps (a) to (c), that may be used in connection with the present invention may e.g. be agarose (sepharose, superose) dextran (sephadex), polypropylene, methacrylate cellulose, polystyrene/divinyl benzene, or the like. The resin materials may be present in different cross-linked forms, depending on the specific use.

The volume of the resin, the length and diameter of the column to be used, as well as the dynamic capacity and flow-rate depend on several parameters such as the volume of fluid to be treated, concentration of protein in the fluid to be subjected to the process of the invention, etc. Determination of these parameters for each step is well within the average skills of the person skilled in the art.

In a preferred embodiment of the present purification process, one or more ultrafiltration steps are performed. Ultrafiltration is useful for removal of small organic molecules and salts in the eluates resulting from previous chromatrographic steps, to equilibrate the Fc-containing protein in the bulk buffer, or to concentrate the Fc-containing protein to the desired concentration. Such ultrafiltration may e.g. be performed on ultrafiltration membranes, with pore sizes allowing the removal of components having molecular weights below 5, 10, 15, 20, 25, 30 or more kDa.

Preferably, ultrafiltration is carried out between steps (b) and (c), and/or after step (d). More preferably, two ultrafiltration steps are carried out, one between steps (b) and (c) and one after step (d).

If the protein purified according to the process of the invention is intended for administration to humans, it is advantageous to include one or more steps of virus removal in the process. Preferably, a virus removal filtration step is carried out after step (d). More preferably, the virus removal filtration step is a nanofiltration step where the filter has a nominal pore size of 20 nm. The method of the present invention, and in particular steps (a), (c), (d) in combination with nanofiltration efficiently eliminates virus load to a combined LRV (log reduction value) of up to about 15 to 25.

In order to facilitate storage or transport, for instance, the material may be frozen and thawed before and/or after any purification step of the invention.

In accordance with the present invention, the recombinant Fc-containing protein may be produced in eukaryotic expression systems, such as yeast, insect, or mammalian cells, resulting in glycosylated Fc-containing proteins.

In accordance with the present invention, it is most preferred to express the Fc-containing protein in mammalian cells such as animal cell lines, or in human cell lines. Chinese hamster ovary cells (CHO) or the murine myeloma cell line NS0 are examples of cell lines that are particularly suitable for expression of the Fc-containing protein to be purified. The Fc-containing protein can also preferably be produced in human cell lines, such as e.g. the human fibrosarcoma HT1080 cell line, the human retinoblastoma cell line PERC6, or the human embryonic kidney cell line 293, or a permanent amniocyte cell line as described e.g. in EP 1 230 354.

If the Fc-containing protein to be purified is expressed by mammalian cells secreting it, the starting material of the purification process of the invention is cell culture supernatant, also called harvest or crude harvest. If the cells are cultured in a medium containing animal serum, the cell culture supernatant also contains serum proteins as impurities.

Preferably, the Fc-containing protein expressing and secreting cells are cultured under serum-free conditions. The Fc-containing protein may also be produced in a chemically defined medium. In this case, the starting material of the purification process of the invention is serum-free cell culture supernatant that mainly contains host cell proteins as impurities. If growth factors are added to the cell culture medium, such as insulin, for example, these proteins will be eliminated during the purification process as well.

In order to create soluble, secreted Fc-containing protein, that are released into the cell culture supernatant, either the natural signal peptide of the therapeutic moiety of the Fc-containing protein is used, or preferably a heterologous signal peptide, i.e. a signal peptide derived from another secreted protein being efficient in the particular expression system used, such as e.g. the bovine or human Growth Hormone signal peptide, or the immunoglobulin signal peptide.

As mentioned above, a preferred Fc-containing protein to be purified in accordance with the present invention is a fusion protein having a therapeutic moiety derived from human TACI (SEQ ID NO: 2), and in particular a fragment derived from its extracellular domain (amino acids 1 to 165 of SEQ ID NO: 2). A preferred fragment comprises amino acids 30 to 110 of SEQ ID NO: 2. In the following, therapeutic moieties derived from the extracellular domain of TACI will be called "soluble TACI" or "sTACI". A preferred Fc-moiety comprises SEQ ID NO: 3, resulting in an Fc-fusion protein according to SEQ ID NO: 4, in the following called "TACI-Fc". The term TACI-Fc, as used herein, also encompasses muteins of TACI-Fc.

The term "muteins", as used herein, refers to analogs of sTACI or TACI-Fc, in which one or more of the amino acid residues of sTACI or TACI-Fc are replaced by different amino acid residues, or are deleted, or one or more amino acid residues are added to the original sequence of sTACI or TACI-Fc without changing considerably the activity of the resulting products as compared with the original sTACI or TACI-Fc. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to the complement of a DNA or RNA, which encodes a sTACI or TACI-Fc according to any of SEQ ID NOs: 2 or 4 under stringent conditions. An example for a DNA sequence encoding a TACI-Fc is SEQ ID NO: 7.

The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

In another embodiment, any such mutein has at least 50%, at least 60%, at least 70%, at least 75%, at least 80%, at least 85%, at least 90%, or at least 95% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990).

Any such mutein preferably has a sequence of amino acids sufficiently duplicative of that of sTACI or TACI-Fc, such as to have substantially similar ligand binding activity as a protein of SEQ ID NO: 2 or 4. For instance, one activity of TACI is its capability of binding to Blys or APRIL (Hymowitz et al., 2006). As long as the mutein has substantial APRIL or Blys binding activity, it can be considered to have substantially similar activity to TACI. Thus, it can be easily determined by the person skilled in the art whether any given mutein has substantially the same activity as a protein of SEQ ID NO: 2 or 4 by means of routine experimentation.

Preferred changes for muteins in accordance with the present invention are what are known as "conservative" substitutions. Conservative amino acid substitutions of sTACI or TACI-Fc, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, under twenty, or preferably under ten, and do not remove or displace amino acids which are critical to a functional conformation, e.g., cysteine residues. Proteins and muteins produced by such deletions and/or insertions come within the purview of the present invention.

Preferably, the conservative amino acid groups are those defined in Table 2. More preferably, the synonymous amino acid groups are those defined in Table 3; and most preferably the synonymous amino acid groups are those defined in Table 4.

TABLE 2

Preferred Groups of Synonymous Amino Acids

| Amino Acid | Synonymous Group |
| --- | --- |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 3

More Preferred Groups of Synonymous Amino Acids

| Amino Acid | Synonymous Group |
| --- | --- |
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 4

Most Preferred Groups of Synonymous Amino Acids

| Amino Acid | Synonymous Group |
| --- | --- |
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

A functional derivative may be prepared from an Fc-fusion protein purified in accordance with the present invention. "Functional derivatives" as used herein cover derivatives of the Fc-containing protein to be purified in accordance with the present invention, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of the unmodified Fc-containing protein as defined above, and do not confer toxic properties on compositions containing it.

Functional derivatives of an Fc-containing protein can e.g. be conjugated to polymers in order to improve the properties of the protein, such as the stability, half-life, bioavailability, tolerance by the human body, or immunogenicity. To achieve this goal, the Fc-containing protein may be linked e.g. to polyethylene glycol (PEG). PEGylation may be carried out by known methods, described in WO 92/13095, for example.

Functional derivatives may also, for example, include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

In a third aspect, the invention relates to a protein purified by the process of purification according to the invention. In the following, such protein is also called "purified Fc-containing protein".

Such purified Fc-containing protein is preferably highly purified Fc-containing protein. Highly purified Fc-fusion protein is determined e.g. by the presence of a single band in a silver-stained, non-reduced SDS-PAGE-gel after loading of protein in the amount of 2 mcg per lane. Purified Fc-fusion protein may also be defined as eluting as a single peak in HPLC.

The Fc-containing protein preparation obtained from the purification process of the invention may contain less than 20% of impurities, preferably less than 10%, 5%, 3%, 2% or 1% of impurities, or it may be purified to homogeneity, i.e. being free from any detectable proteinaceous contaminants contaminants as determined e.g. by silver stained SDS-PAGE or HPLC, as explained above.

Purified Fc-containing protein may be intended for therapeutic use, in particular for administration to human patients. If purified Fc-containing protein is administered to patients, it is preferably administered systemically, and preferably subcutaneously or intramuscularly, or topically, i.e. locally. Rectal or intrathecal administration may also be suitable, depending on the specific medical use of purified Fc-containing protein.

For this purpose, in a preferred embodiment of the present invention, the purified Fc-containing protein may be formulated into pharmaceutical composition, i.e. together with a pharmaceutically acceptable carrier, excipients or the like.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The therapeutically effective amounts of the active protein(s) will be a function of many variables, including the type of Fc-containing protein, the affinity of the Fc-containing protein for its ligand, the route of administration, the clinical condition of the patient.

A "therapeutically effective amount" is such that when administered, the Fc-containing protein results in inhibition of its ligand of the therapeutic moiety of the Fc-fusion protein, as explained above and referring particularly to Table 5 above.

The dosage administered, as single or multiple doses, to an individual will vary depending upon a variety of factors, including pharmacokinetic properties of the Fc-fusion protein, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of the natural ligand of the therapeutic moiety in an individual.

Purified Fc-containing protein may be used in an amount of 0.001 to 100 mg/kg or 0.01 to 10 mg/kg or body weight, or 0.1 to 5 mg/kg of body weight or 1 to 3 mg/kg of body weight or 2 mg/kg of body weight.

In further preferred embodiments, the purified Fc-containing protein is administered daily or every other day or three times per week or once per week.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

The present invention further relates to the use of cation exchange chromatography for the reduction of the concentration of free Fc-moieties in a composition comprising an Fc-containing protein.

In a preferred embodiment, the concentration of free Fc is reduced to less than 20% or less than 15% or less than 10% or less than 5% or less than 2% or less than 1% or less than 0.8% or less than 0.5% or less than 0.2% or less than 0.1% of the total protein concentration of said composition.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Purification of Recombinant, Human TACI-Fc from Serum-Free Cho Cell Supernatant

Glossary Used in all Examples

| | |
|---|---|
| BV: | bed volume |
| CHO: | Chinese Hamster Ovary |
| DSP: | Downstream Process |
| EDTA: | Ethylene Diamine Tetraacetic Acid |
| ELISA: | Enzyme-Linked ImmunoSorbent Assay |
| HAC: | Hydroxyapatite Chromatography |
| HCP: | Host Cell Protein |
| HPLC: | High Performance Liquid Chromatography |
| id: | internal diameter |
| K: | potassium |
| kD: | kilo Dalton |
| MES: | 2-Morpholinoethanesulfonic acid |
| Na: | sodium |
| NaAc: | Sodium Acetate |
| n/d: | not determined |
| PA-SE-HPLC: | Protein A Size-Exclusion High Performance Liquid Chromatography |
| ppm: | parts per million |
| RO: | Reverse Osmosis |
| RT: | Room Temperature |
| SDS-PAGE: | Sodium Dodecyl Sulphate Polyacrylamide Gel Electrophoresis |
| SE-HPLC: | Size-Exclusion High Performance Liquid Chromatography |
| T° C.: | Temperature |
| TMAC: | Tetra-Methyl Ammonium Chloride |
| UV: | Ultra-Violet |
| WFI: | Water For Injection |
| WRO | Water Reverse Osmosis |

Example 1

Capture Step: Affinity purification on Protein A

Starting material was clarified harvest of a TACI-Fc expressing CHO cell clone cultured under serum-free conditions and stored frozen until use.

The Capture Step on a MabSelect Xtra™ column (GE Healthcare 17-5269-03) was carried out according to the following protocol, on a column having a bed height of 17 cm. All operations were performed at room temperature, except for the load solution, which was kept at a temperature below 15° C. The UV signal at 280 nm was recorded.

Sanitization

The column was sanitised with at least 3 BV of 0.1M acetic acid+20% ethanol in reverse flow at 250 cm/h. The flow was stopped for 1 hour.

Wash Step

The column was washed with at least 2 BV of RO water in reverse flow at 250 cm/h.

Equilibration

The column was equilibrated with at least 5 BV of 25 mM sodium phosphate+150 mM NaCl pH7.0 (until conductivity and pH parameters are within specified range: pH 7.0±0.1, conductivity 18±2 mS/cm) in down flow at 450 cm/h.

Loading

The column was loaded with clarified harvest kept at a temperature below 15° C. to a capacity of up to 15 mg total TACI-Fc as determined by Biacore assay per ml of packed resin at a flow rate of 350 cm/h.

Wash Step

Wash the column with at least 2 BV of equilibration buffer at 350 cm/h then with at least 4 BV of equilibration buffer (until the UV signal is back to baseline) at 450 cm/h.

Elution

The material was eluted with different elution buffers as shown in Table I at a flow rate of 350 cm/h. The eluate fraction was collected from start of UV signal increase to 6.0±0.5 BV of elution. The eluate was incubated for 1 hour at room temperature at a pH below 4.1 (adjused by addition of citric acid solution, if necessary) and then the pH was adjusted to 5.0±0.1 by addition of 32% NaOH solution.

Regeneration

The column was regenerated with at least 3 BV of 50 mM NaOH+1M NaCl in reverse flow at 450 cm/h, stop the flow for 15 min then re-start the flow at 450 cm/h for at least 3 BV (until the UV signal is back to baseline).

From this step, the column was operated in reverse flow mode.

Wash Step

The column was washed with at least 2 BV of RO water at 450 cm/h.

Sanitation

The column was santitised with at least 3 BV of sanitisation buffer at 250 cm/h, the flow stopped and the column incubated for 60 min.

Final Wash Steps

The column was washed with at least 1 BV of RO water at 250 cm/h, then with at least 3 BV of equilibration buffer at 250 cm/h and finally with at least 2 BV of RO water at 250 cm/h.

Finally, the column was stored after flushing with at least 3 BV of 20% ethanol at 250 cm/h.

Results

TABLE I

Results using different elution buffers

| Run # | Elution buffer | TACI-Fc yield (%) | Aggregates (%) | HCPs (ppm) |
|---|---|---|---|---|
| 1 | 50 mM NaAc pH 3.7 | 47.7 | 30.3 | 5558 |
| 2 | 100 mM NaAc pH 3.8 | 55.7 | 25.2 | n/d |
| 3 | 200 mM NaAc pH 3.8 | 58.0 | 28.2 | n/d |
| 4 | 100 mM NaAc pH 3.7 | 68 | 30.0 | n/d |
| 5 | 0.2M NaAc + 150 mM NaCl pH 4 | 75.1 | 3.8 | n/d |
| 6 | 100 mM NaAc pH 3.7 | 84.6 | 22 | 3491 |
| 7 | 250 mM NaAc pH 3.7 | 82.8 | 18.7 | 3318 |
| 8 | 100 mM Na citrate pH 3.7 | 79.2 | 8.8 | 4710 |
| 9 | 250 mM Na citrate pH 3.7 | 71.9 | 23 | 2347 |
| 10 | 100 mM Na citrate pH 3.75 | 82.8 | 8.5 | 1576 |
| 11 | 100 mM Na citrate pH 3.75 | 66.6 | 9.0 | 664 |
| 12 | 100 mM NaAc pH 3.85 | 83.3 | 15.0 | n/d |
| 13 | 100 mM Na citrate pH 3.75 | 81.0 | 9.1 | 3490 |
| 14 | 100 mM Na citrate pH 3.65 | 75.1 | 14.6 | 2580 |
| 14 | 100 mM Na citrate pH 3.75 | 44.7 | 18.4 | 3783 |
| 16 | 100 mM Na citrate pH 3.75 | 47.1 | 15.8 | 3217 |
| 17 | 100 mM Na citrate pH 3.75 | 50.7 | 9.4 | 2349 |
| 18 | 100 mM Na citrate pH 3.75 | 58.0 | 10.4 | 2550 |
| 19 | 100 mM Na citrate pH 3.75 | 67.1 | 28.7 | 2372 |
| 20 | 100 mM Na citrate pH 3.75 | 65.6 | 17.5 | 2353 |
| 21 | 100 mM Na citrate pH 3.75 | 75.6 | 19.4 | 1807 |
| 22 | 100 mM Na citrate pH 3.75 | 57.1 | 20.7 | 2465 |
| 23 | 100 mM Na citrate pH 3.75 | 51.9 | 18.4 | 2030 |
| 24 | 100 mM Na citrate pH 3.75 | 58 | 11.5 | 1746 |
| 25 | 100 mM Na citrate pH 3.75 | 41.8 | 22.9 | 3029 |
| 26 | 100 mM Na citrate pH 3.9 | 39.4 | 6.0 | 2424 |
| 27 | 100 mM Na citrate pH 3.9 | 31.0 | 8.8 | 2936 |
| 28 | 100 mM Na Ac pH 4.1 | 28.3 | 25.0 | 3311 |
| 29 | 100 mM Na citrate pH 3.9 | 46.4 | 9.1 | n/d |
| 30 | 100 mM NaAc pH 4.1 | 42.8 | 13.4 | n/d |

TABLE I-continued

Results using different elution buffers

| Run # | Elution buffer | TACI-Fc yield (%) | Aggregates (%) | HCPs (ppm) |
|---|---|---|---|---|
| 31 | 100 mM Na citrate pH 3.75 | 57.5 | 26.5 | n/d |
| 32 | 100 mM NaAc pH 4.2 | 38.1 | 10.1 | n/d |
| 33 | 100 mM Na citrate pH 3.9 | 43.3 | 8.3 | 2011 |
| 34 | 100 mM Na citrate pH 3.9 | 63.6 | 6.6 | 1749 |
| 35 | 100 mM Na citrate pH 3.9 | 65.7 | 7.3 | 1689 |
| 36 | 100 mM Na citrate pH 3.9 | 62.7 | 7.4 | 1609 |
| 37 | 100 mM Na citrate pH 3.9 | 61.6 | 7.4 | 1479 |
| 38 | 100 mM Na citrate pH 3.9 | 60.6 | 7.4 | 1623 |
| 39 | 100 mM Na citrate pH 3.9 | 64.6 | 8.0 | 1497 |

Conclusions

TACI-Fc5 in clarified harvest was captured directly on a MabSelect Xtra column at a dynamic capacity of 15 g total TACI-Fc5 per L of packed resin at a flow rate of 350 cm/h. Elution conditions, especially pH, were optimized to maximize recovery of product while providing significant reduction in aggregate levels. An elution buffer of 0.1 M sodium citrate pH 3.9 was selected giving about 5-10% aggregate levels starting from about 25-40% in clarified harvest and with no turbidity observed. HCP levels were typically 1500-2000 ppm. The HCP levels were measured by ELISA using polyclonal antibodies. The antibod mixture w generated against host cell proteins derived from clarified and concentrated cell culture supernatant of non-transfected CHO cells.

Example 2

Cation Exchange Chromatography

The eluate from the capture step on Protein A, dialysed into suitable loading buffer, was used as a starting material for the cation exchange chromatography.

A Fractogel EMD $SO_3^-$ column (Merck 1.16882.0010) having a bed height of 10 cm was used in this step. A Fractogel $SO_3^-$ column with a bed height of 15 cm may be used as well. In the latter case, the dynamic capacity and flow rate may need adaptation, which is well within routine knowledge of the person skilled in the art. All the operations were performed at room temperature and the flow rate was kept constant at 150 cm/h. The UV signal at 280 nm was recorded at all time.

Wash Step

The column was washed with at least 1 BV of WRO (water reverse osmosis).

Sanitisation

Then, the column was sanitised with at least 3 BV of 0.5M NaOH+1.5M NaCl in up-flow mode.

Rinsing

The column was rinsed with at least 4 BV of WRO in down-flow mode.

Equilibration

The column was equilibrated with at least 4 BV of 100 mM sodium citrate pH5.0 (or until the target conductivity of 12±1 mS/cm and pH 5.0±0.1 are reached).

Loading

The column was loaded with post capture material at pH 5.0 (pH at 5.0±0.1, conductivity at 12±1 mS/cm) and at a capacity of no more than 50 mg TACI-Fc, as determined by SE-HPLC assay per ml of packed resin.

Wash Step

The column was then washed with at least 5 BV of 100 mM sodium phosphate pH6.5.

Elution

The column was eluted with different buffers and under different conditions as reported in tables II-IV below.

Regeneration and Sanitisation

The column was regenerated and sanitised with 4 BV of 0.5M NaOH+1.5M NaCl in up-flow mode. Then, the flow was stopped for 30 min.

Rinsing

The column was rinsed with at least 4 BV of WRO.

Storing

The column was stored in at least 3 BV of 20% ethanol.

Results

TABLE II

Effect of elution pH and conductivity
HCP levels in the load: 189 ppm

| pH | Conductivity (mS/cm) | TACI-Fc recovery | HCPs (ppm) | HCP clearance (x) |
|---|---|---|---|---|
| 6.5 | 15.0 | 25% | 118 | 1.6 |
| 7.3 | 22.5 | 100% | 50 | 3.8 |
| 8.0 | 15.0 | 95% | 34 | 5.5 |
| 7.3 | 22.5 | 100% | 56 | 3.4 |
| 7.3 | 33.0 | 98% | 133 | 1.4 |
| 7.3 | 22.5 | 96% | 45 | 4.2 |
| 7.3 | 22.5 | 97% | 53 | 3.6 |
| 7.3 | 12.0 | 54% | 79 | 2.4 |
| 6.3 | 22.5 | 83% | 47 | 4.1 |
| 8.0 | 30.0 | 96% | 108 | 1.8 |
| 8.2 | 22.5 | 97% | 46 | 4.2 |
| 6.5 | 30.0 | 91% | 116 | 1.6 |
| 7.3 | 22.5 | 93% | 48 | 3.9 |
| 7.3 | 22.5 | 95% | 40 | 4.8 |

Table III shows the TACI-Fc recovery and HCP clearance when loading at a capacity of 10 and 32 mg TACI-Fc per ml of resin and eluting in a phosphate buffer at a conductivity of between 12 to 33 mS/cm. Collection of the peak was done from the beginning of the UV increase for 10±0.5 BV.

TABLE III

Effect of optimal elution pH and conductivity when loading at capacity HCP levels in load: 201 ppm

| Loading capacity (mg/ml) | pH | Conductivity (mS/cm) | TACI-Fc recovery | HCPs (ppm) | HCP clearance (x) |
|---|---|---|---|---|---|
| 10 | 8.0 | 15.0 | 91% | 67 | 3.0 |
|  |  | 20.7 | 93% | 61 | 3.3 |
| 32 | 8.0 | 20.7 | 88% | 54 | 3.7 |

Table IV shows the effect of a wash step with 50 or 100 or 150 mM sodium phosphate pH 6.5 on TACI-Fc recovery and HCP clearance.

TABLE IV

Effect of wash step conditions on column performance
HCP levels in the load: 190 ppm and aggregate levels: 2.0%

| Sodium Phosphate concentration in wash (mM) | TACI-Fc yield in wash | TACI-Fc yield in eluate | Aggregates in eluate | HCPs in eluate (ppm) |
|---|---|---|---|---|
| wash 1 | 50 | 0.7% | 99% | 2.8% | 62 |
| wash 2 | 100 | 2.1% | 98% | 2.9% | 59 |
| wash 3 | 150 | 9.1% | 90% | 2.7% | 49 |

The buffer used in wash 2, containing 100 mM sodium phosphate pH 6.5, had a conductivity of 8.4 mS/cm.

FIG. 1 shows a silver stained, non-reduced SDS-PAGE gel of samples derived from experiments using the three wash step conditions shown in Table IV on the free Fc clearance.

Figure 2:
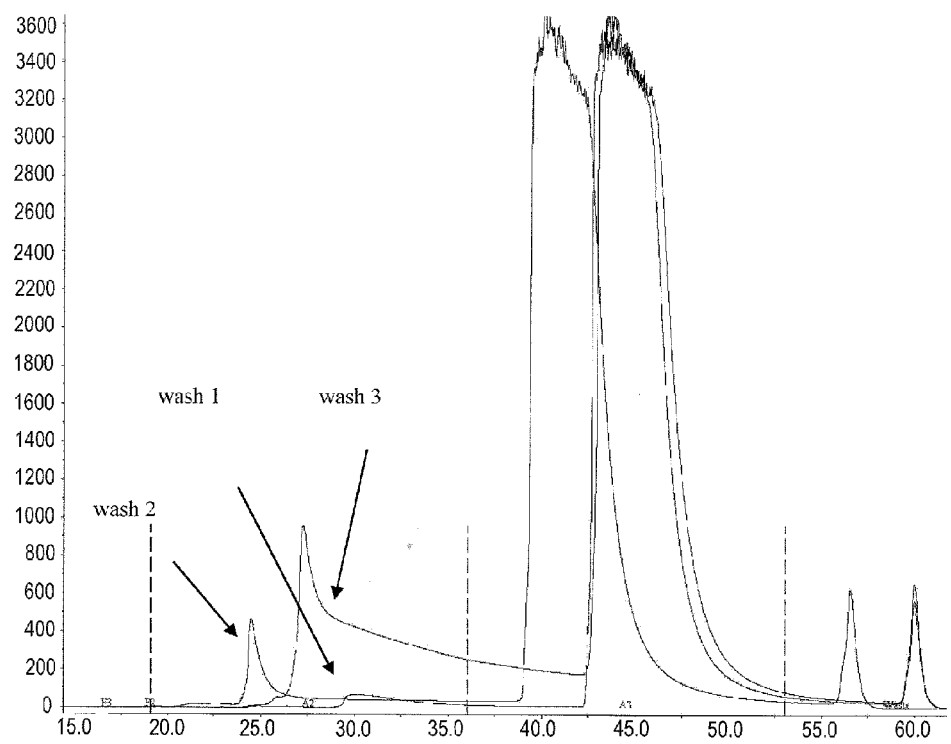
FIG. 2 shows the chromatographic profile of the cation exchange chromatography described in Example 2.

FIG. 2 shows overlapping chromatograms of the wash step experiments with sodium phosphate at different concentrations.

The wash step was optimized at pH 6.5 with increasing concentrations of sodium phosphate (50 to 150 mM). As can be seen in FIG. 1, a wash buffer concentration of 150 mM (wash 3, lane 6) resulted in losses of TACI-Fc. A wash buffer concentration of 50 mM (wash 1, lane 8) resulted in a peak of pure TACI-Fc, however, the eluate contained traces of free Fc. A wash step with 100 mM sodium phosphate pH 6.5 resulted in 98% recovery in the main peak of elution and only 2% losses in the wash (FIG. 2). HCP clearance was 3.2 fold. Analysis of wash and eluate fractions by SDS-PAGE show that the wash step contained Free Fc with some intact TACI-Fc at buffer concentrations of 100 mM or above (FIG. 1, lanes 4 and 6). A concentration of 100 mM or more is necessary to completely remove Free Fc from the eluate fraction (FIG. 1, lanes 5 and 7).

Conclusions

A cation-exchange step was developed as a second purification step, after the capture step. The capture eluate was at low pH (5.0) and low conductivity and could be directly loaded onto the cation-exchanger. A Fractogel EMD $SO_3^-$ resin was selected with a loading capacity of 50 mg/ml. The non-bioactive degradation product free Fc could be efficiently removed in a wash step with 0.1 M sodium phosphate pH 6.5. Elution conditions were optimised for best clearance of HCPs and high TACI-Fc recovery (179 mM sodium phosphate pH 8.0, conductivity 20.7 mS/cm).

Alternatively, elution can be carried out in 10 BV of 20 mM sodium phosphate and 180 mM NaCl pH8.0 from the start of the rise in absorbance at 280 nm.

Example 3

Anion Exchange Chromatography

The starting material used for this purification step was the eluate from the cation exchange step on Fractogel $SO^-_3$ (see Example 2), dialysed or diluted into suitable loading buffer.

This anion-exchange chromatography step was carried out on a SOURCE 30Q column (GE Healthcare 17-1275-01) with a bed height of 10 cm. A SOURCE 30Q column with a bed height of 15 cm may be used as well in this step. In the latter case, the dynamic capacity and flow rate may need adaptation, which is well within routine knowledge of the person skilled in the art.

All operations were carried out at room temperature and the UV signal at 280 nm was recorded. The steps were carried out at a flow rate of either 150 or 200 cm/h.

Rinsing

First, the column was rinsed with at least 1 BV of RO water at a flow rate of 150 cm/h.

Sanitisation

Then, the column was sanitised with at least 3 BV of 0.5M NaOH+1.5M NaCl.

Wash Step

The column was washed with at least 3 BV, preferably 4 to 10 BV, of 0.5M Na phosphate pH 7.5 at a flow rate of 200 cm/h.

Equilibration

The column was equilibrated with at least 5 BV of 10, 15, 20, 25, or 30 mM sodium phosphate pH 7.5. Optionally, the column can be pre-equilibrated with 3 BV of 0.5M sodium phosphate pH7.5.

Loading, washing and concomitant collection of TACI-Fc in the flow-through

The column was loaded with post-cation exchange material diluted to obtain a phosphate concentration of 10 to 30 mM, pH 7.5, at a capacity of no more than 50 mg TACI-Fc as determined by SE-HPLC assay per ml of packed resin, collecting the flow-through from start of UV increase until the end of the wash step, which is carried out in 4±0.5 BV of equilibration buffer.

Regeneration/Sanitisation

The column was regenerated and sanitised with at least 3 BV of 0.5M NaOH+1.5M NaCl in reverse flow mode (until UV signal is back to the baseline) at a flow rate of 150 cm/h. At the end of the regeneration, the pump is stopped for 30 min.

Wash Step

The column was washed with at least 3 BV of RO water at a flow rate of 200 cm/h.

Storing

The column is stored in at least 3 BV of 20% ethanol (v/v) at a flow rate of 150 cm/h.

Results

The following Table V summarizes the results obtained with the purification process described above.

TABLE V

Effect of loading phosphate concentration

| Load pH | Load phosphate conc (mM) | Load TACI-Fc conc (mg/L) | Load capacity (mg/ml) | TACI-Fc recovery | Aggregates | HCPs (ppm) |
|---|---|---|---|---|---|---|
| 7.5 | 30 | 773 | 39 | 94% | 10.4% | 82.8 |
| 7.5 | 25 | 639 | 39 | 90% | 6.9% | 50.4 |
| 7.5 | 20 | 651 | 49 | 90% | 5.6% | 43.9 |
| 7.5 | 15 | 437 | 46 | 88% | 3.4% | 45.0 |
| 7.5 | 10 | 283 | n./d. | 82% | 2.8% | 26.3 |

Conclusions

The anion-exchange step on a Source 30 Q column in flow-through mode was optimised to maximise clearance of HCPs and aggregates. Loading cation-exchange eluate either diluted or diafiltered in 20 mM sodium phosphate buffer at pH7.5 gave the best compromise between product recovery (90%) and clearance of HCPs (from about 2000 ppm to 44 ppm) and aggregates (from about 25% to 5.6%). Dynamic capacity of 50 mg TACI-Fc per ml of packed resin at a flow rate of 150-200 cm/h was used.

Example 4

Hydroxyapatite Chromatography

The starting material used for this purification step was anion-exchange chromatography flow-through (see Example 3).

A CHT Ceramic Hydroxyapatite Type I, 40 μm column (Biorad 157-0040) with a bed height of 10 cm was used.

All operations were carried out at room temperature. The flow rate was kept constant at 175 cm/h and the UV signal at 280 nm was recorded. All solutions were sterile filtered and the equipment sanitised with sodium hydroxide before use. The column was stored in 0.5M NaOH solution when not in use.

Initial Wash Steps (Rinsing and Pre-Equilibration)

The column was washed with at least 1 BV of 20 mM sodium phosphate pH7.5 buffer, and then with at least 3 BV of 0.5M sodium phosphate buffer pH7.5 to lower the pH.

Equilibration

The column was equilibrated with at least 5 BV of 20 mM sodium phosphate pH7.5 (or until the target conductivity of 3.0±0.3 mS/cm and pH 7.5±0.1 were reached).

Loading

The column was loaded with the SOURCE 30Q flow-through with calcium chloride added to 0.1 mM final concentration from a stock solution at 0.5M and pH adjusted to 7.0 by addition of 85% ortho-phosphoric acid, at a capacity of NMT 50 mg TACI-Fc as determined by SE-HPLC assay per ml of packed resin. It is also possible to load the SOURCE 30Q flow-through without calcium chloride, adjusted to pH 7.0, on the hydroxyapatite column.

Wash Steps

The column was washed with at least 4 BV of 3, 4 or 5 mM sodium phosphate, 10 mM MES, 0.1 mM $CaCl_2$ pH6.5. it is also possible to use the same buffer without calcium chloride.

Elution

The column was eluted with 5, 4, 3 or 2 mM sodium phosphate (see Table VI), 10 mM MES, 0.1 mM $CaCl_2$, and 0.6, 0.7, 0.8 or 0.9 M KCl pH 6.5 buffer (see Table VII) from the beginning of the UV increase for different BV (see Tables VI and VII). It is also possible to use the same buffer without calcium chloride for the elution.

Rinsing

The column was rinsed with:
at least 1 BV of 20 mM sodium phosphate pH7.5 buffer;
at least 3 BV of 0.5M sodium phosphate pH7.5 buffer; and
with at least 1 BV of 20 mM sodium phosphate pH7.5 buffer.

Storing

The column was stored in at least 3 BV of 0.5M NaOH.

Results

Table VI shows the effect of phosphate concentration (from 2 to 5 mM) in the elution buffer on the clearance of aggregates and product recovery. Elution peak fractions were pooled and analysed by SE-HPLC for TACI-Fc concentration and aggregate levels.

TABLE VI

Effect of phosphate concentration in the elution buffer

| Phosphate conc (mM) | BV of elution | TACI-Fc yield | Aggregates |
|---|---|---|---|
| 5 | 12 | 73% | 0.49% |
|   | 13 | 74% | 0.52% |
|   | 14 | 68% | 0.65% |
|   | 15 | 77% | 0.67% |
|   | 16 | 77% | 0.70% |
|   | 17 | 70% | 0.73% |
|   | 18 | 76% | 0.85% |
| 4 | 12 | 68% | 0.34% |
|   | 13 | 67% | 0.29% |
|   | 14 | 66% | 0.36% |
|   | 15 | 67% | 0.39% |
|   | 16 | 66% | 0.38% |
|   | 17 | 66% | 0.32% |
|   | 18 | 66% | 0.40% |
| 3 | 12 | 70% | 0.46% |
|   | 13 | 76% | 0.42% |
|   | 14 | 73% | 0.51% |

TABLE VI-continued

Effect of phosphate concentration in the elution buffer

| Phosphate conc (mM) | BV of elution | TACI-Fc yield | Aggregates |
|---|---|---|---|
|   | 15 | 71% | 0.52% |
|   | 16 | 69% | 0.55% |
|   | 17 | 69% | 0.50% |
|   | 18 | 70% | 0.53% |
| 2 | 12 | 65% | 0.19% |
|   | 13 | 66% | 0.00% |
|   | 14 | 66% | 0.18% |
|   | 15 | 68% | 0.14% |
|   | 16 | 66% | 0.17% |
|   | 17 | 71% | 0.19% |
|   | 18 | 65% | 0.16% |

Table VII shows the effect of KCl concentration in the elution buffer on the clearance of aggregates and product recovery. Two sodium phosphate concentrations were investigated: 2 and 3 mM. Elution peak fractions were pooled and analysed by SE-HPLC for TACI-Fc concentration and aggregate levels.

TABLE VII

Effect of potassium chloride concentration in the elution buffer

| Phosphate conc (mM) | KCl conc (M) | BV of elution | TACI-Fc yield | aggregates |
|---|---|---|---|---|
| 3 | 0.6 | 10 | 102% | 0.48% |
|   |   | 11 | 109% | 0.46% |
|   |   | 12 | 106% | 0.43% |
|   |   | 13 | 105% | 0.42% |
|   |   | 14 | 103% | 0.43% |
| 3 | 0.7 | 10 | 96% | 0.42% |
|   |   | 11 | 97% | 0.40% |
|   |   | 12 | 98% | 0.41% |
|   |   | 13 | 96% | 0.40% |
|   |   | 14 | 96% | 0.43% |
| 3 | 0.8 | 10 | 106% | 0.58% |
|   |   | 11 | 110% | 0.55% |
|   |   | 12 | 112% | 0.57% |
|   |   | 13 | 101% | 0.59% |
|   |   | 14 | 110% | 0.57% |
| 2 | 0.6 | 10 | 71% | 0.29% |
|   |   | 11 | 79% | 0.28% |
|   |   | 12 | 80% | 0.29% |
|   |   | 13 | 80% | 0.29% |
|   |   | 14 | 81% | 0.26% |
| 2 | 0.9 | 10 | 64% | 0.27% |
|   |   | 11 | 72% | 0.25% |
|   |   | 12 | 73% | 0.29% |
|   |   | 13 | 70% | 0.33% |
|   |   | 14 | 66% | 0.24% |

Conclusions:

Hydroxyapatite chromatography provides a reliable, efficient way of reducing TACI-Fc aggregate levels. Starting from anion-exchange chromatography purified material (see Example 3) with aggregate levels of about 5-8%, hydroxyapatite chromatography can reduce these levels to below 0.8% with a recovery of TACI-Fc of 85-90%.

References

1. Akerstrom and Bjork, J Biol. Chem. 1989 Nov. 25; 264 (33):19740-6.
2. Altschul S F et al, J Mol Biol, 215, 403-410, 1990
3. Altschul S F et al, Nucleic Acids Res., 25:389-3402, 1997
4. Armour K L. et al., 1999. Recombinant human IgG molecules lacking Fcgamma receptor I binding and monocyte triggering activities. Eur. J. Immunol. 29(8):2613-24
5. Bodmer et al., TIBS 27(1), 19-24

6. Boschetti, E., Jungbauer, Sep. Sci. & Tech. 2 No. 15, Acad. Press (2000) 53
7. Boschetti et al., Genetic Engineering Vol. 20, No. 13, July, 2000
8. Bossen et al., JBC 281(2), 13964-13971
9. Bram and von Büllow, U.S. Pat. No. 5,969,102 (1999)
10. Bram et al., WO 98/39361
11. Carter P J., 2006. Potent antibody therapeutics by design. Nature Reviews Immunology. Advance online publication
12. Devereux J et al, Nucleic Acids Res, 12, 387-395, 1984
13. Feng et al., Bioprocessing 2005, 1-7
14. Giovannini, Biotechnology and Bioengineering 73:522-529 (2000)
15. Grantham et al., Science, Vol. 185, pp. 862-864 (1974)
16. Gross et al., Nature 404(27), 995-999
17. Gross et al., WO 00/40716
18. Hinton P R. et al., 2004. Engineered human IgG antibodies with longer serum half-lives in primates. J Biol. Chem. 279(8):6213-6
19. Hymowitz et al., JBC 280(8), 7218-7227
20. Idusogie E E. et al., 2000. Mapping of the C1q binding site on rituxan, a chimeric antibody with a human IgG1 Fc. J. Immunol. 164(8):4178-84
21. Idusogie E E. et al., 2001. Engineered antibodies with increased activity to recruit complement. J. Immunol. 166 (4):2571-5
22. Kabat, E. A., Wu, T. T., Perry, H. M., Gottesman, K. S., and Foeller, C. (1991), Sequences of Proteins of Immunological Interest, 5th Ed., National Institutes of Health, Bethesda, Md.
23. Kochanek et al., EP 1 230 354
24. Locksley et al., Cell 104, 487-501, 2001
25. Melchers, Ann. Rheum. Dis 2003, 62, 25-27.
26. Moore et al., Science 285: 260-3
27. Moreau et al., Blood 103(8), 3148-3157
28. Naismith and Sprang, TIBS 23, 74-79, 1998
29. Novak et al., Blood 103(2), 689-694
30. Parker et al., WO 02/094852
31. Pearson, Methods Enzymol. 1990; 183:63-98
32. Porath, J. Carlsson, I. Olsson, and G. Belfrage, Nature (London) 258, 598-599 (1975)
33. Porath and B. Olin, Biochemistry 22, 1621-1630 (1983)
34. Puren et al., Proc Natl Acad Sci USA. 1999 Mar. 2; 96(5):2256-61
35. Shepard, J. of Chromatography 891:93-98 (2000)
36. Shields R L. et al., 2001. High resolution mapping of the binding site on human IgG1 for Fc gamma R1, Fc gamma R11, Fc gamma RIII, and FcRn and design of IgG1 variants with improved binding to the Fc gamma R. J Biol. Chem. 276(9):6591-604.
37. Smith et al., WO 91/03553
38. Smith et al., WO 94/06476
39. Stanker, J. Immunological Methods 76:157-169 (1985) (10 mM to 30 mM sodium phosphate elusion gradient)
40. Steurer W. et al., 1995. Ex vivo coating of islet cell allografts with murine CTLA4/Fc promotes graft tolerance. J. Immunol. 155(3):1165-74
41. Sun et al., WO 2005/044856
42. Tarditi, J. Chromatography 599:13-20 (1992)
43. Vaccaro C. et al., 2005. Engineering the Fc region of immunoglobulin G to modulate in vivo antibody levels. Nat. Biotechnol. 23(10):1283-8
44. Vigers et al., Nature. 1997 Mar. 13; 386(6621):190-4
45. Vedantham et al., WO 03/59935
46. Vola et al., BioTechniques 14:650-655 (1993)
47. von Bülow and Bram, Science 228: 138 (1997)
48. Xia et al., J. Exp. Med. 2000, 137-143.

The invention claimed is:

1. A method for reducing the content of free Fc-moieties in a fluid comprising an Fc-containing protein and free Fc-moieties and having a pH of at least one unit below the isoelectric point (pI) of the Fc-containing protein, the method comprising cation exchange chromatography comprising the steps of loading said fluid onto a cation exchange resin to absorb the Fc-containing protein, washing the cation exchange resin with a first buffer having a conductivity of 8.2 to 9.2 mS/cm and a pH of 6.0 to 7.0 to remove free Fc-moieties, and eluting the Fc-containing protein with a second buffer to produce an eluate comprising the Fc-containing protein, whereby the level of free Fc-moieties in said eluate relative to the level of Fc-containing protein has been reduced from said fluid by a factor of 5 to 15.

2. The method according to claim 1, wherein the first buffer has a conductivity of 8.2 to 8.6 mS/cm.

3. The method according to claim 1 or 2, wherein the first buffer comprises 75 to 125 mM sodium phosphate.

4. The method according to claim 1, wherein the second buffer has a pH ranging from 7.0 to 8.5.

5. The method according to claim 4, wherein the second buffer has a conductivity of 15 to 22 mS/cm.

6. The method according to claim 1 or 4, wherein the cation exchange resin is a strong cation exchange resin.

7. The method according to claim 6, wherein the cation exchange resin comprises $SO_3^-$ groups.

8. The method according to claim 6, wherein the resin comprises a cross-linked methacrylate matrix.

9. The method according to claim 1 or 4, further comprising a purification step selected from affinity chromatography, anion exchange chromatography and hydroxyapatite chromatography.

10. The method according to claim 1 or 4, wherein the Fc-containing protein comprises an Immunoglobulin (Ig) constant region.

11. The method according to claim 10, wherein the constant region is a human constant region.

12. The method according to claim 10, wherein the immunoglobulin is an $IgG_1$.

13. The method according to claim 10, wherein the constant region comprises a CH2 and a CH3 domain.

14. The method according to claim 1 or 4, wherein the Fc-containing protein comprises an immunoglobulin variable region.

15. The method according to claim 14, wherein the Fc-containing protein is an antibody.

16. The method according to claim 1 or 4, wherein the Fc-containing protein is an Fc-fusion protein.

17. The method according to claim 16, wherein the Fe-fusion protein comprises an extracellular domain of a member of the tumor necrosis factor receptor (TNFR) superfamily selected from the group consisting of TNFR1 and TNFR2.

18. The method according to claim 16, wherein the Fe-fusion protein comprises an extracellular domain of BAFF-R, BCMA, or TACI.

19. The method according to claim 16, wherein the Fe-fusion protein comprises a polypeptide selected from
   a. amino acids 30 to 110 of SEQ ID NO: 2;
   b. SEQ ID NO: 3; and
   c SEQ ID NO: 4.

20. The method according to claim 1, wherein free Fc-moieties constitute less than 5% of the total protein concentration of said eluate.

21. The method according to claim 1, wherein free Fc-moieties constitute less than 2% of the total protein concentration of said eluate.

22. The method according to claim 1, wherein free Fc-moieties constitute less than 1% of the total protein concentration of said eluate.

23. The method according to claim 1, wherein free Fc-moieties constitute less than 0.5% of the total protein concentration of said eluate.

24. The method according to claim 1, wherein free Fc-moieties constitute less than 0.2% of the total protein concentration of said eluate.

25. The method according to claim 1, wherein free Fc-moieties constitute less than 0.1% of the total protein concentration of said eluate.

26. The method according to claim 9, wherein said fluid comprising an Fc-containing protein is an eluate from an affinity chromatography purification step.

27. The method according to claim 26, wherein said eluate having a reduced level of free Fc-moieties is subjected to anion exchange chromatography to produce an anion exchange chromatography flow-through comprising the Fc-containing protein.

28. The method according to claim 27, wherein the anion exchange chromatography flow-through comprising the Fc-containing protein is subjected to hydroxyapatite chromatography to produce a hydroxyapatite chromatography eluate comprising the Fc-containing protein.

29. The method according to claim 1, wherein the first buffer has a conductivity of 8.4 to 9.2 mS/cm.

\* \* \* \* \*

UNITED STATES PATENT AND TRADEMARK OFFICE
CERTIFICATE OF CORRECTION

PATENT NO. : 8,513,393 B2
APPLICATION NO. : 12/377122
DATED : August 20, 2013
INVENTOR(S) : Eon-Duval et al.

It is certified that error appears in the above-identified patent and that said Letters Patent is hereby corrected as shown below:

IN THE CLAIMS

Claim 1, column 39, line 20: Delete "Fe-containing" and insert --Fc-containing--.
Claim 1, column 39, line 21: Delete "Fe-moieties" and insert --Fc-moieties--.
Claim 1, column 39, line 22: Delete "Fe-containing" and insert --Fc-containing--.
Claim 15, column 39, lines 54-55: Delete "Fe-containing" and insert --Fc-containing--.
Claim 17, column 40, lines 10-11: Delete "Fe-fusion" and insert --Fc-fusion--.
Claim 18, column 40, lines 14-15: Delete "Fe-fusion" and insert --Fc-fusion--.
Claim 19, column 40, lines 17-18: Delete "Fe-fusion" and insert --Fc-fusion--.
Claim 23, column 40, lines 31-32: Delete "Fe-moieties" and insert --Fc-moieties--.
Claim 24, column 40, lines 34-35: Delete "Fe-moieties" and insert --Fc-moieties--.

Signed and Sealed this
Twenty-ninth Day of March, 2016

Michelle K. Lee
*Director of the United States Patent and Trademark Office*